(12) United States Patent
Kawakami

(10) Patent No.: US 7,488,849 B2
(45) Date of Patent: Feb. 10, 2009

(54) BENZIDINE DERIVATIVE, AND LIGHT-EMITTING DEVICE AND ELECTRIC APPLIANCE USING THE BENZIDINE DERIVATIVE AS THE HOLE TRANSPORTING MATERIAL

(75) Inventor: Sachiko Kawakami, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 11/570,215

(22) PCT Filed: Jun. 2, 2005

(86) PCT No.: PCT/JP2005/010543

§ 371 (c)(1),
(2), (4) Date: Dec. 7, 2006

(87) PCT Pub. No.: WO2005/121064

PCT Pub. Date: Dec. 22, 2005

(65) Prior Publication Data

US 2007/0219398 A1   Sep. 20, 2007

(30) Foreign Application Priority Data

Jun. 10, 2004   (JP)   ............... 2004-172051

(51) Int. Cl.
*C07C 211/54* (2006.01)
(52) U.S. Cl. ...................... 564/309; 428/917
(58) Field of Classification Search ............ None
See application file for complete search history.

(56) References Cited

U.S. PATENT DOCUMENTS

| 7,164,155 | B2 | 1/2007 | Yamazaki et al. |
| 7,226,332 | B2 | 6/2007 | Arai et al. |
| 2004/0263066 | A1 | 12/2004 | Abe et al. |
| 2006/0061265 | A1 | 3/2006 | Kawamura et al. |

FOREIGN PATENT DOCUMENTS

WO   WO 03/048225 A2   6/2003
WO   WO 2004/020373 A1   3/2004

*Primary Examiner*—Brian J Davis
(74) *Attorney, Agent, or Firm*—Fish & Richardson P.C.

(57) ABSTRACT

According to the present invention, a material that can be used as a hole transporting material is provided. Further, a material that is easily kept in a non-crystalline state and can be used as a hole transporting material is also provided. One embodiment of the present invention is a compound represented by a general formula (1). In the general formula (1), $R^1$ is hydrogen or an alkyl group having 1-4 carbon atoms. Further, one embodiment according to the present invention is a hole transporting material containing the compound represented by the general formula (1).

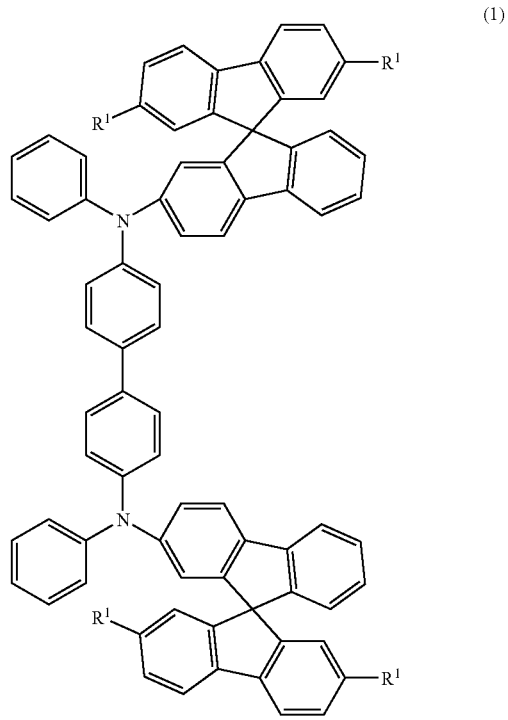

(1)

14 Claims, 15 Drawing Sheets

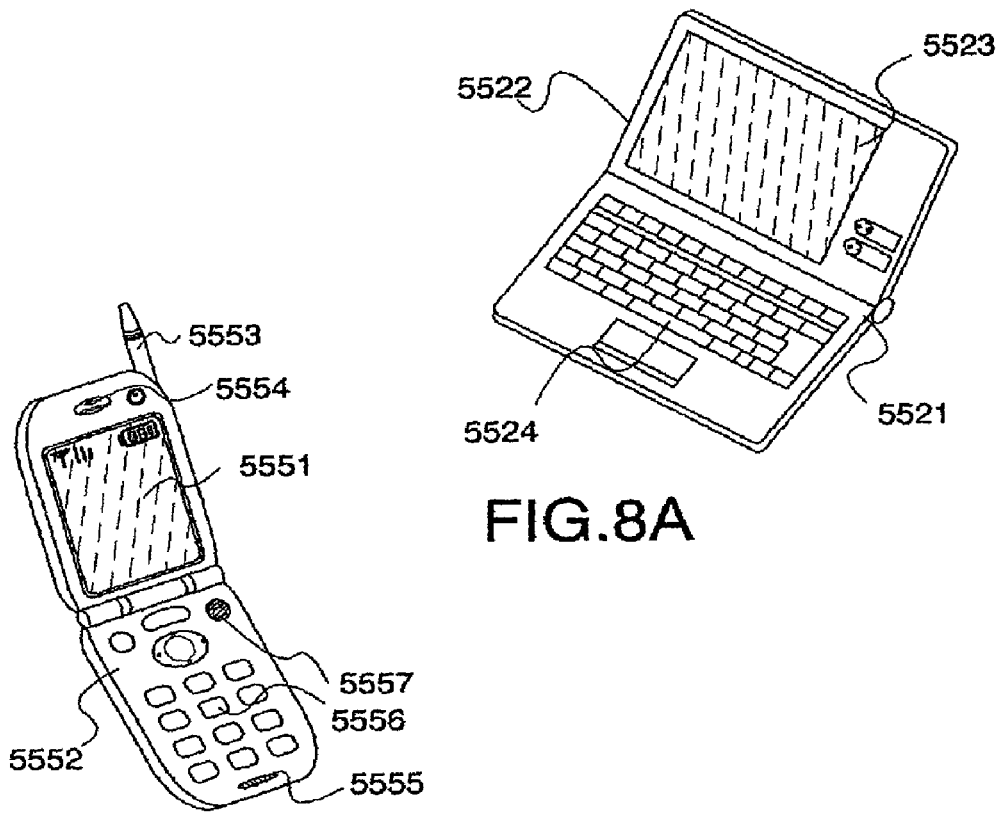
FIG.8A
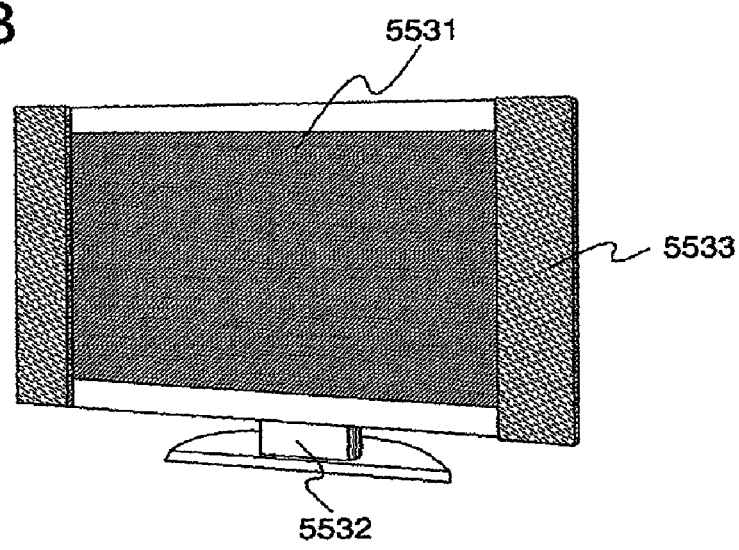
FIG.8B
FIG.8C

BENZIDINE DERIVATIVE, AND LIGHT-EMITTING DEVICE AND ELECTRIC APPLIANCE USING THE BENZIDINE DERIVATIVE AS THE HOLE TRANSPORTING MATERIAL

TECHNICAL FIELD

The present invention relates to a material that can be used as a material for manufacturing a light-emitting element.

BACKGROUND ART

In recent years, most light-emitting elements utilized in a display or the like have structures in which a layer containing a light-emitting material is interposed between a pair of electrodes. In such the light-emitting element, electrons injected from one electrode and holes injected from the other electrode are recombined with each other to form excitons to emit light while returning the excitons to the ground state.

In the field of a light-emitting element, a material for manufacturing the light-emitting element that has high emission efficiency, good chromaticity, less deterioration, and long life time has been studied in diverse ways.

As one of the contributing factors in the deterioration of the light-emitting element, the crystallization of a material that constitutes the light-emitting element can be nominated. Therefore, a material that is difficult to be crystallized has been developed, for example, an organic material that has high glass-transition temperature and excellent heat resistance was disclosed in WO Publication No.

DISCLOSURE OF INVENTION

It is an object of the present invention to provide a material that has excellent heat resistance and that can be used as a hole transporting material. It is another object of the present invention to provide a material that is easily kept in a non-crystalline state and can be used as a hole transporting material.

One embodiment of the present invention is a benzidine derivative represented by a general formula (1).

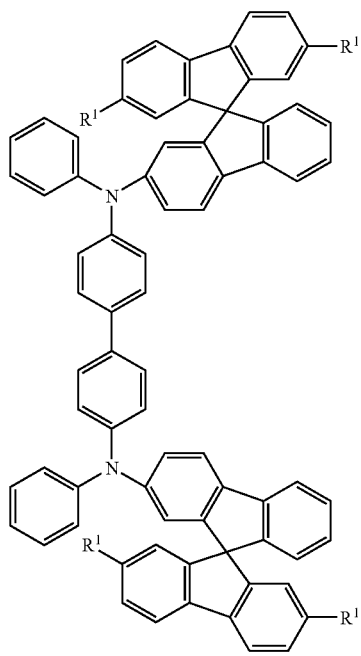

wherein $R^1$ is hydrogen or an alkyl group having 1-4 carbon atoms.

One embodiment of the present invention is a hole transporting material containing the benzidine derivative represented by the general formula (1).

One embodiment of the present invention is a compound that is obtained by the coupling reaction of N,N'-diphenylbenzidine with 2-bromo-spiro-9,9'-bifluorene or 2-bromo-2',7'-dialkyl-spiro-9,9'-bifluorene and that has a melting point of from 323 to 324° C.

One embodiment of the present invention is a hole transporting material containing a compound that is obtained by the coupling reaction of N,N'-diphenylbenzidine with 2-bromo-spiro-9,9'-bifluorene or 2-bromo-2',7'-dialkyl-spiro-9,9'-bifluorene and that has a melting point of from 323 to 324° C.

One embodiment of the present invention is a light-emitting element having a layer containing the benzidine derivative represented by the foregoing general formula (1).

One embodiment of the present invention is the light-emitting element having the layer containing the compound that is obtained by the coupling reaction of N,N'-diphenylbenzidine with 2-bromo-spiro-9,9'-bifluorene or 2-bromo-2',7'-dialkyl-spiro-9,9'-bifluorene.

According to the present invention, a benzidine derivative having excellent heat resistance can be obtained. Further, a benzidine derivative that is easily kept in a non-crystalline state can be obtained according to the present invention.

According to the present invention, a hole transporting material having excellent heat resistance can be obtained. Further, a hole transporting material that is easily kept in a non-crystalline state can be obtained according to the present invention.

Since the benzidine derivative according to the present invention has excellent heat resistance, a light-emitting element that is hardly changed its characteristics due to heat can be obtained by using the benzidine derivative according to the present invention. Since the benzidine derivative according to the present invention can be easily kept in a non-crystalline state, a light-emitting element hardly deteriorated due to crystallization can be obtained by using the benzidine derivative according to the present invention.

BRIEF DESCRIPTION OF DRAWINGS

FIGS. 8A to 8C are views for showing electric appliances;

BEST MODE FOR CARRYING OUT THE INVENTION

Hereinafter, one embodiment of the present invention is explained. As the present invention may be embodied in several forms, it is to be understood that various changes and modifications will be apparent to those skilled in the art without departing from the spirit of essential characteristics of the present invention. Therefore, unless otherwise such changes and modifications depart from the scope of the present invention hereinafter described, they should be construed as being included therein.

Embodiment 1

One embodiment of the present invention is a benzidine derivative represented by structural formulae (2) to (5).

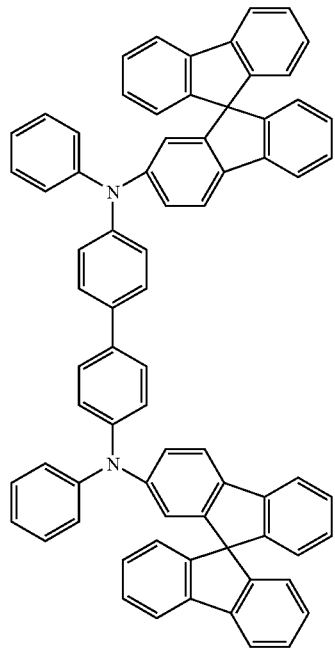

(2)

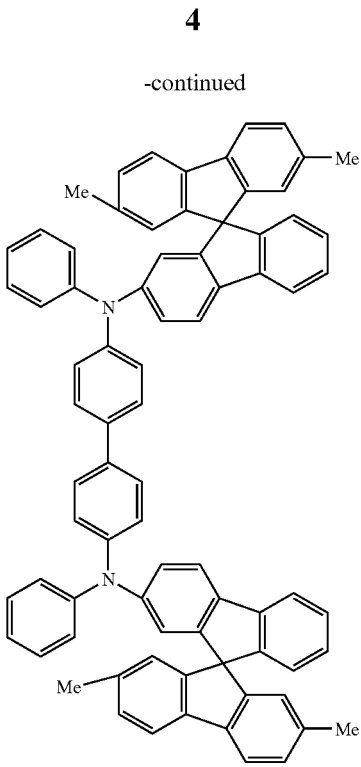

(3)

-continued

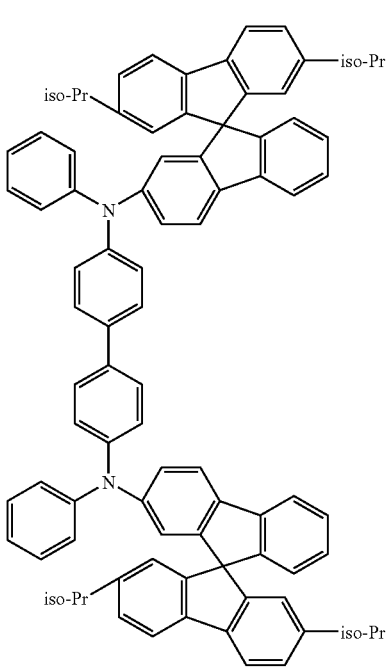

(4)

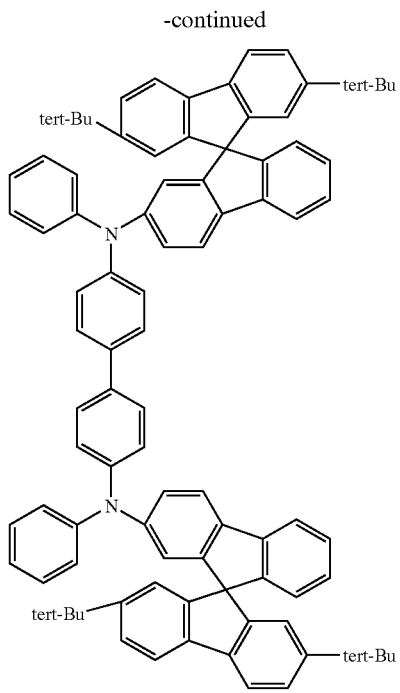

(5)

The benzidine derivatives represented by structural formulae (2) to (5) have high glass-transition temperature and excellent heat resistance. Further, the benzidine derivatives represented by structural formulae (2) to (5) are difficult to be crystallized.

Although a synthesis method of the benzidine derivative according to the present invention is not especially limited, the benzidine derivative can be synthesized by a coupling reaction of N,N'-diphenylbenzidine with 2-bromo-spiro-9,9'-bifluorene or 2-bromo-2',7'-dialkyl-spiro-9,9'-bifluorene as represented by a synthesis scheme (a-1).

(a-1)

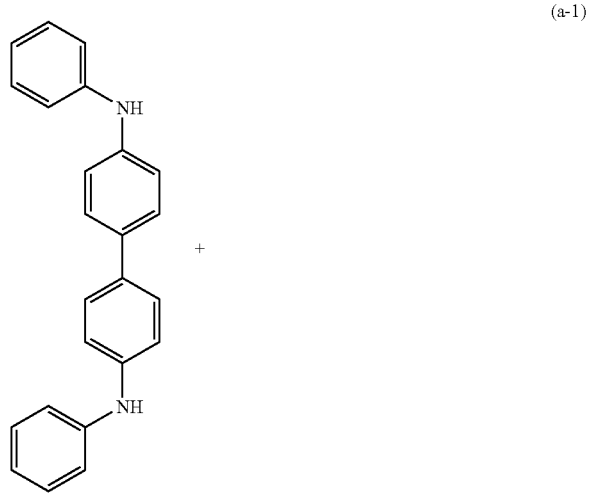

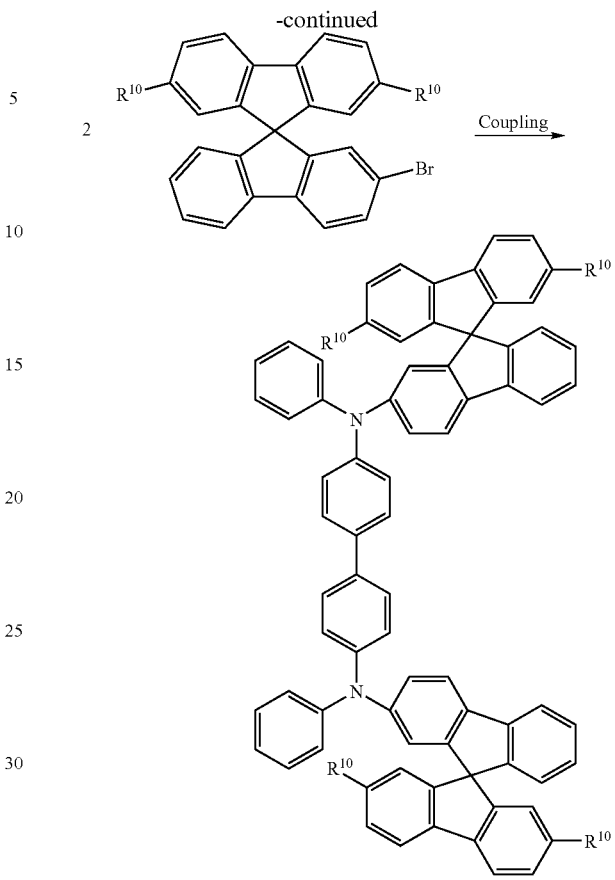

In the synthesis scheme (a-1), $R^{10}$ is hydrogen or an alkyl group having 1-4 carbon atoms. Here, an alkyl group having 3 or 4 carbon atoms is preferably in the state of branching.

The benzidine derivative according to the present invention as noted above can be used as a material for forming a hole transporting layer, that is, a hole transporting material.

Embodiment 2

An embodiment of a light-emitting element that uses the benzidine derivative according to the present invention as a hole transporting material is explained with reference to FIG. 1.

Figure 1:
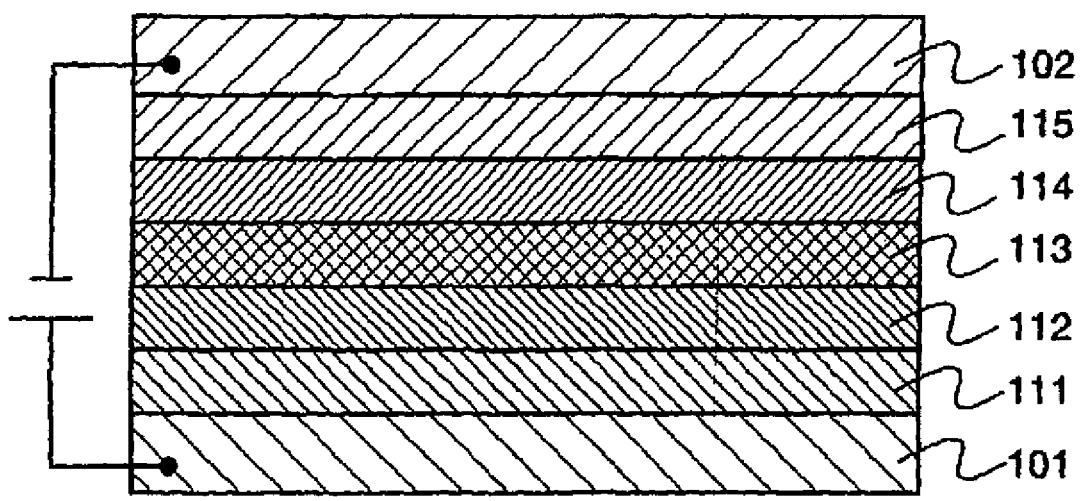
FIG. 1 is an explanatory view of one embodiment of a light-emitting element according to the present invention.

FIG. 1 illustrates a light-emitting element that includes a light-emitting layer 113 interposed between a first electrode 101 and a second electrode 102.

In such the light-emitting element, holes injected from the first electrode 101 and electrons injected from the second electrode 102 are recombined within the light-emitting layer 113 to make a light-emitting material be an excited state. Then, the light-emitting material in an excited state emits light while returning to the ground state. In the light-emitting element according to this embodiment, the first electrode 101 serves as an anode, and the second electrode 102 serves as a cathode. The light-emitting material is a material that has good emission efficiency and can emit light at a desired light emission wavelength.

Although the light-emitting layer 113 is not especially limited, the light-emitting layer is preferably formed by dispersing the light-emitting material within a layer made from a material having a larger energy gap than that of the light-emitting material. Accordingly, quenching of light emitted from the light-emitting material depending on density can be prevented. The energy gap refers to an energy gap between a LUMO level and a HOMO level.

The light-emitting material is not especially limited. A material that has good light emission efficiency and that can emit light at a desired light emission wavelength may be used as the light-emitting material. For instance, in the case that reddish light emission is required, a material that exhibits light emission having a peak of an emission spectrum at from 600 to 680 nm such as 4-dicyanomethylene-2-isopropyl-6-[2-(1,1,7,7-tetrametyljulo lidine-9-yl)ethenyl]-4H-pyrane (abbreviated as DCJTI), 4-dicyanomethylene-2-methyl-6-[2-(1,1,7,7-tetramethyljuloli dine-9-yl)ethenyl]-4H-pyrane (abbreviated as DCJT), 4-dicyanomethylene-2-tert-butyl-6-[2-(1,1,7,7-tetramethyljulolidine-9-yl)ethenyl]-4-H-pyrane (abbreviated as DCJTB), periflanthene, or 2,5-dicyano-1,4-bis[2-(10-methoxy-1,1,7,7-tetramethyljuloli dine-9-yl)ethenyl]benzene can be used. In the case that greenish emission is required, a material that exhibits light emission having a peak of an emission spectrum at from 500 to 550 nm such as N,N'-dimethylquinacridon (abbreviated as DMQd), coumarin 6, coumarin 545T, or tris(8-quinolinolato)aluminum (abbreviated as $Alq_3$) can be used. In the case that bluish emission is required, a material that exhibits light emission having a peak of an emission spectrum at from 420 to 500 nm such as 9,10-bis(2-naphthyl)-tert-butylanthracene (abbreviated as t-BuDNA), 9,9'-biantryl, 9,10-diphenylanthracene (abbreviated as DPA), 9,10-bis(2-naphthyl)anthracene (abbreviated as DNA), bis(2-methyl-quinolinolato)-4-phenylphenolato-gallium (abbreviated as BGaq), or bis(2-methyl-8-quinolinolato)-4-phenylphenolato-aluminum (BAlq) can be used.

A material used for making the light-emitting material be a dispersion state is not especially limited, for example, an anthracene derivative such as 9,10-di(2-naphthyl)-2-tert-buthylanthracene (abbreviated as t-BuDNA), a carbazole derivative such as 4,4'-bis(N-carbazolyl)biphenyl (abbreviated as CBP), a metallic complex such as bis [2-(2-hydroxyphenyl)pyridinato]zinc (abbreviated as $Znpp_2$), or bis [2-(2-hydroxyphenyl)benzoxazolato]zinc (abbreviated as ZnBOX) can be used.

The first electrode 101 is not especially limited, but preferably formed by a material having a large work function in the case of serving as an anode as in this embodiment. Specifically, indium tin oxide (ITO), indium tin oxide containing silicon oxide, indium oxide containing zinc oxide of from 2 to 20%, gold (Au), platinum (Pt), nickel (Ni), tungsten (W), chromic (Cr), molybdenum (Mo), iron (Fe), cobalt (Co), copper (Cu), palladium (Pd), and the like can be used. Further, the first electrode 101 can be formed by using a sputtering method, a vapor deposition method, or the like.

The second electrode 102 is not especially limited, but preferably formed by material having a small work function in the case of serving as a cathode as in this embodiment. Specifically, aluminum (Al) containing alkali metal, alkali earth metal, or the like such as lithium (Li) or magnesium (Mg) is preferably used. Alternatively, the foregoing indium tin oxide (ITO) or the like can be used. Further, the second electrode 102 can be formed by using a sputtering method, a vapor deposition method, or the like.

In order to extract light to the outside, either or both of the first electrode 101 and the second electrode are preferably an electrode made from indium tin oxide or the like, or an electrode formed to have a thickness of several to several ten nm so that visible light can pass therethrough.

A hole transporting layer 112 is interposed between the first electrode 101 and the light-emitting layer 113 as shown in FIG. 1. The hole transporting layer serves to transport holes injected from the first electrode 101 to the light-emitting layer 113. As noted above, the hole transporting layer 112 is provided to be separated the first electrode 101 from the light-emitting layer 113, which leads to prevent quenching due to metal.

The hole transporting layer 112 is not especially limited, but preferably formed by the benzidine derivative according to the present invention represented by a general formula (1) or structural formulae (2) to (4). The benzidine derivative according to the present invention has high heat resistance. Therefore, the hole transporting layer 112 that is hardly changed its characteristics due to heat can be formed by using the benzidine derivative according to the present invention as a hole transporting material. In addition, the benzidine derivative according to the present invention is difficult to be crystallized. Hence, the hole transporting layer 112 that is difficult to be crystallized can be formed by using the benzidine derivative according to the present invention as a hole transporting material.

Further, the hole transporting layer 112 may be formed to have a multiple layered structure by stacking two or more layers made from the benzidine derivative according to the present invention represented by the general formula (1) or the structural formulae (2) to (4).

As shown in FIG. 1, an electron transporting layer 114 may be formed between the second electrode 102 and the light-emitting layer 113. The electron transporting layer refers to a layer serving to transport electrons injected from the second electrode 102 to the light-emitting layer 113. As noted above, the electron transporting layer 114 is provided to separate the second electrode 102 from the light-emitting layer 113, which leads to prevent quenching due to metal.

An electron transporting layer 114 is not especially limited, a metal complex having a quinoline skeleton or a benzoquinoline skeleton such as tris(8-quinolinolato)aluminum (abbreviated as $Alq_3$), tris(5-methyl-quinolinolato)aluminum (abbreviated as $Almq_3$), bis(10-hydroxybenzo[h]-quinolinato) beryllium (abbreviated as $BeBq_2$), or bis(2-methyl-8-quinolinolato)-4-phenylphenolato-aluminum (abbreviated as BAlq) is preferably used. Alternatively, a metal complex having an oxazole or thiazole series ligand such as bis[2-(2-hydroxyphenyl)-benzoxazolato]zinc (abbreviated as $Zn(BOX)_2$) or bis[2-(2-hydroxyphenyl)-benzothiazolato] zinc (abbreviated as $Zn(BTZ)_2$) can be used. Besides, 2-(4-biphenylyl)-5-(4-tert-butylphenyl)-1,3,4-oxadiazole (abbreviated as PBD), 1,3-bis[5-(p-tert-butylphenyl)-1,3,4-oxadiazole-2-yl]benzene (abbreviated as OXD-7), 3-(4-tert-butylphenyl)-4-phenyl-5-(4-biphenylyl)-1,2,4-tria zole (abbreviated as TAZ), 3-(4-tert-butylphenyl)-4-(4-ethylphenyl)-5-(4-biphenylyl)-1,2,4-triazole (abbreviated as p-EtTAZ), bathophenanthroline (abbreviated as BPhen), bathocuproin (abbreviated as BCP), or the like can be used. The electron transporting layer 114 is preferably formed by the foregoing material having higher mobility of electrons than that of holes. The electron transporting layer 114 is more preferably formed by a material having electron mobility of $10^{-6}$ $cm^2/Vs$ or more. The electron transporting layer 114 may be formed to have a multiple layered structure by stacking two or more layers made from the foregoing materials.

Further, a hole injecting layer 111 may be formed between the first electrode 101 and the hole transporting layer 112 as shown in FIG. 1. The hole injecting layer refers to a layer that serves to assist in the injection of holes from an electrode serving as an anode to the hole transporting layer 112.

The hole injecting layer 111 is not especially limited. As a material for the hole injecting layer 111, metal oxide such as molybdenum oxide (MoOx), vanadium oxide (VOx), ruthenium oxide (RuOx), tungsten oxide (WOx), manganese oxide (MnOx) can be used. In addition, a phthalocyanine based compound such as phthalocyanine (abbreviated as $H_2Pc$) or copper phthalocyanine (CuPC), an aromatic amine based compound such as 4,4-bis(N-(4-(N,N-di-m-tolylamino)phenyl)-N-phenylamino)biphenyl (abbreviated as DNTPD), or polymer such as poly(ethylenedioxythiophene)/poly(styrenesulfonic acid)solution (PEDOT/PSS) can be used.

An electron injecting layer 115 may be formed between the second electrode 102 and the electron transporting layer 114 as shown in FIG. 1. The electron injecting layer refers to a layer that assists in injection of electrons from an electrode serving as a cathode to the electron transporting layer 114. In the case that the electron transporting layer is not especially provided, an electron injecting layer can be provided between the electrode serving as a cathode and the light-emitting layer to assist in injection of electrons to the light-emitting layer.

The electron injecting layer 115 is not especially limited. As a material for the electron injecting layer 115, a compound of alkali metal or alkali earth metal such as lithium fluoride (LiF), cesium fluoride (CsF), or calcium fluoride ($CaF_2$) can be used. In addition, a mixture of a material having high electron transporting property such as $Alq_3$ or 4,4-bis(5-methylbenzoxazol-2-yl)stilbene (BzOs) and alkali metal or alkali earth metal such as magnesium or lithium can be used as a material for the electron injecting layer 115.

In the above explained light-emitting element according to the present invention, the hole injecting layer 111, the hole transporting layer 112, the light-emitting layer 113, the electron transporting layer 114, and the electron injecting layer 115 can be respectively formed by a vapor deposition method, an ink jet method, a coating method, or the like. The first electrode 101 or the second electrode 102 can be formed by a sputtering method, a vapor deposition method, or the like.

As noted above, a light-emitting element that is hardly changed its characteristics by characteristics changes of the hole transporting layer due to heat can be formed by forming the hole transporting layer using the benzidine derivative according to the present invention. Further, a light-emitting element that is hardly deteriorated due to the crystallization of the hole transporting layer can be formed by forming the hole transporting layer using the benzidine derivative according to the present invention.

Embodiment 3

A light-emitting element according to the present invention explained in Embodiment 2 can be applied to a pixel portion of a light-emitting device that has a display function or a lighting portion of a light-emitting device that has a lighting function. Since the light-emitting element according to the present invention that is hardly changed its characteristics due to characteristics changes of the hole transporting layer due to heat and hardly deteriorated due to crystallization, a light-emitting device that has hardly defects of an image or illumination due to the deterioration of the light-emitting element can be obtained by using the light-emitting element according to the present invention.

In this embodiment, a circuit structure and a driving method of a light-emitting device having a display function are explained with reference to FIGS. 3 to 6.

Figure 3:
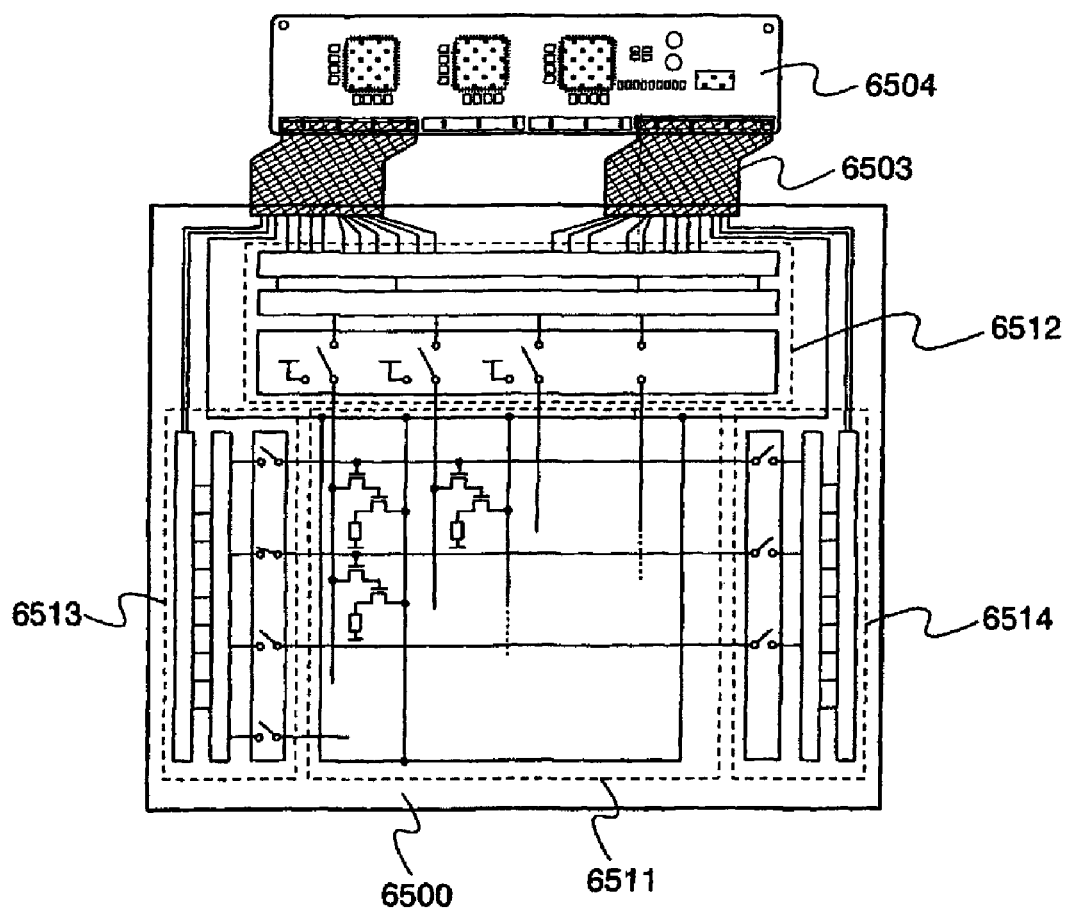
FIG. 3 is an explanatory view of a light-emitting device applied with the present invention.

FIG. 3 is a schematic view of a top surface of a light-emitting device applied with the present invention. In FIG. 3, a pixel portion 6511, a source signal line driver circuit 6512, a gate signal line driver circuit 6513 for writing, and a gate signal line driver circuit 6514 for erasing are provided over a substrate 6500. The source signal line driver circuit 6512, the gate signal line driver circuit 6513 for writing, and the gate signal line driver circuit 6514 for erasing are connected to an FPC (flexible printed circuit) 6503 that is an external input terminal via wiring groups respectively. Each the source signal line driver circuit 6512, the gate signal line driver circuit 6513 for writing, and the gate signal line driver circuit 6514 for erasing receives a video signal, a clock signal, a start signal, a reset signal, and the like from the FPC 6503. Further, the FPC 6503 is attached with a printed wiring board (PWB) 6504. The driver circuit portion and the pixel portion 6511 are not always required to be provided over one substrate. For example, a TCP that is formed by mounting an IC chip onto the FPC provided with a wiring pattern can be used to be provided to the outside of the substrate.

The pixel portion 6511 is provided with a plurality of source signal lines in rows that extends in columns. Current supply lines are arranged in rows. In the pixel portion 6511, a plurality of gate signal lines extended in rows is arranged in columns. Further, a plurality of pairs of circuits including light-emitting elements is arranged in the pixel portion 6511.

Figure 4:
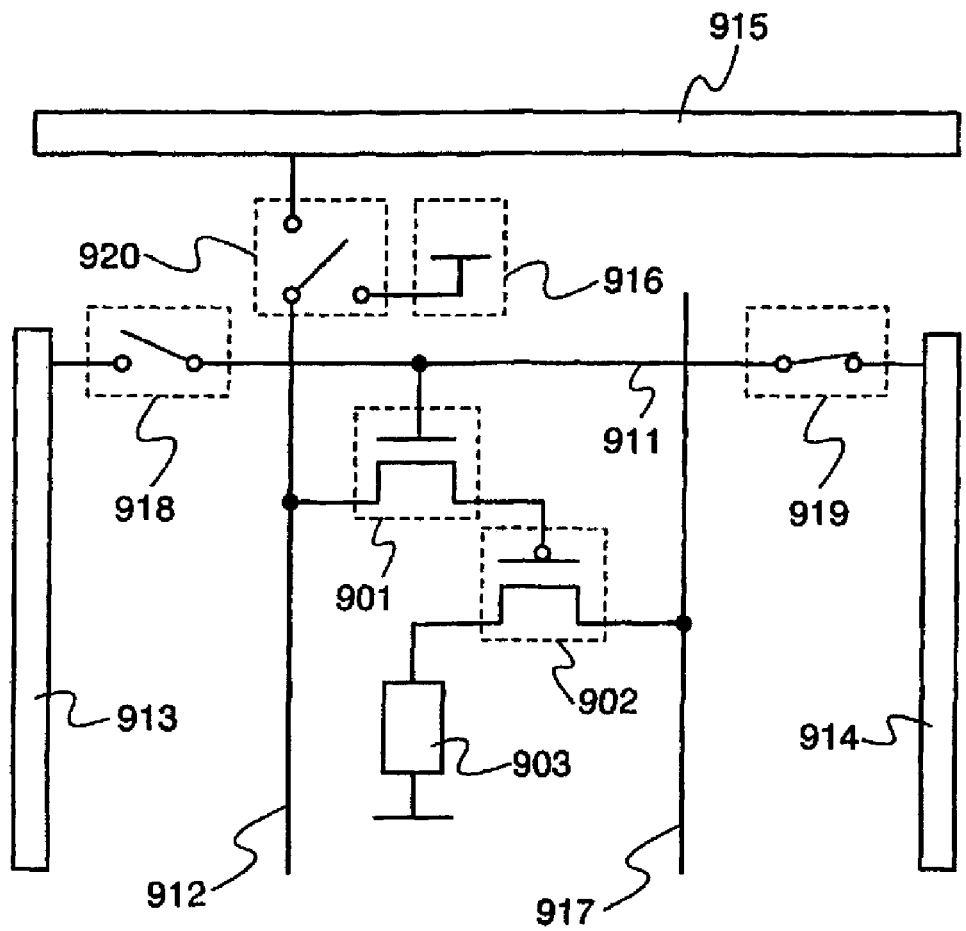
FIG. 4 is an explanatory view of a circuit included in the light-emitting device applied with the present invention.

FIG. 4 is a diagram for illustrating a circuit for operating one pixel. A circuit shown in FIG. 4 includes a first transistor 901, a second transistor 902, and a light-emitting element 903.

Each the first transistor 901 and the second transistor 902 is a three-terminal element including a gate electrode, a drain region, and a source region, in which a channel region is formed between the drain region and the source region. Since the source region and the drain region are varied depending on the structure or the operation condition of the transistor, it is difficult to identify the source region or the drain region. In this embodiment, each electrode connected to a region serving as a source and a region serving as a drain is denoted as a first electrode of the transistor and a second electrode of the transistor.

A gate signal line 911 and a gate signal line driver circuit 913 for writing are electrically connected or disconnected by a switch 918. Further, the gate signal line 911 and a gate signal line driver circuit 914 for erasing are electrically connected or disconnected by a switch 919. A source signal line 912 is electrically connected to either of a source signal line driver circuit 915 or a power source 916 by a switch 920. The gate of the first transistor 901 is electrically connected to the gate signal line 911. The first electrode of the first transistor 901 is electrically connected to the source signal line 912, whereas the second electrode of the first transistor 901 is electrically connected to the gate electrode of the second transistor 902. The first electrode of the second transistor 902 is electrically connected to a current supply line 917, whereas the second electrode of the second transistor 902 is electrically connected to one electrode included in the light-emitting element 903. The switch 918 can be included in the gate signal line driver circuit 913 for writing. The switch 919 can also be included in the gate signal line driver circuit 914 for erasing. Further, the switch 920 can also be included in the source signal line driver circuit 915.

Figure 5:
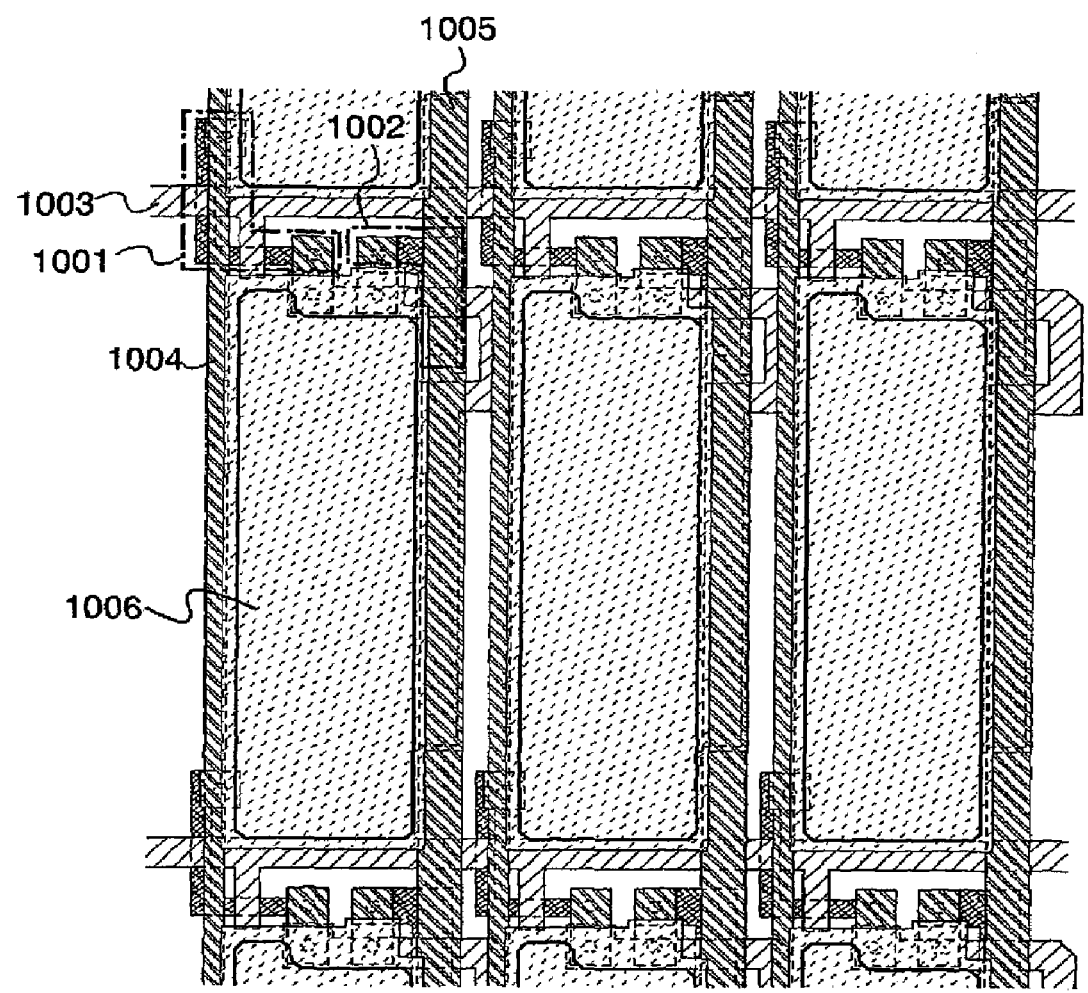
FIG. 5 is a top view of the light-emitting device applied with the present invention.

The arrangement of the transistor, the light-emitting element, and the like in the pixel portion is not especially limited. For instance, the transistor, the light-emitting element, and the like can be arranged as illustrated in a top view of FIG. 5. In FIG. 5, a first electrode of a first transistor 1001 is connected to a source signal line 1004, whereas a second electrode is connected to a gate electrode of a second transistor 1002. The first electrode of the second transistor 1002 is connected to a current supply line 1005, whereas the second electrode of the second transistor 1002 is connected to an electrode 1006 of the light-emitting element. A part of a gate signal line 1003 serves as a gate electrode of the first transistor 1001.

Figure 6:
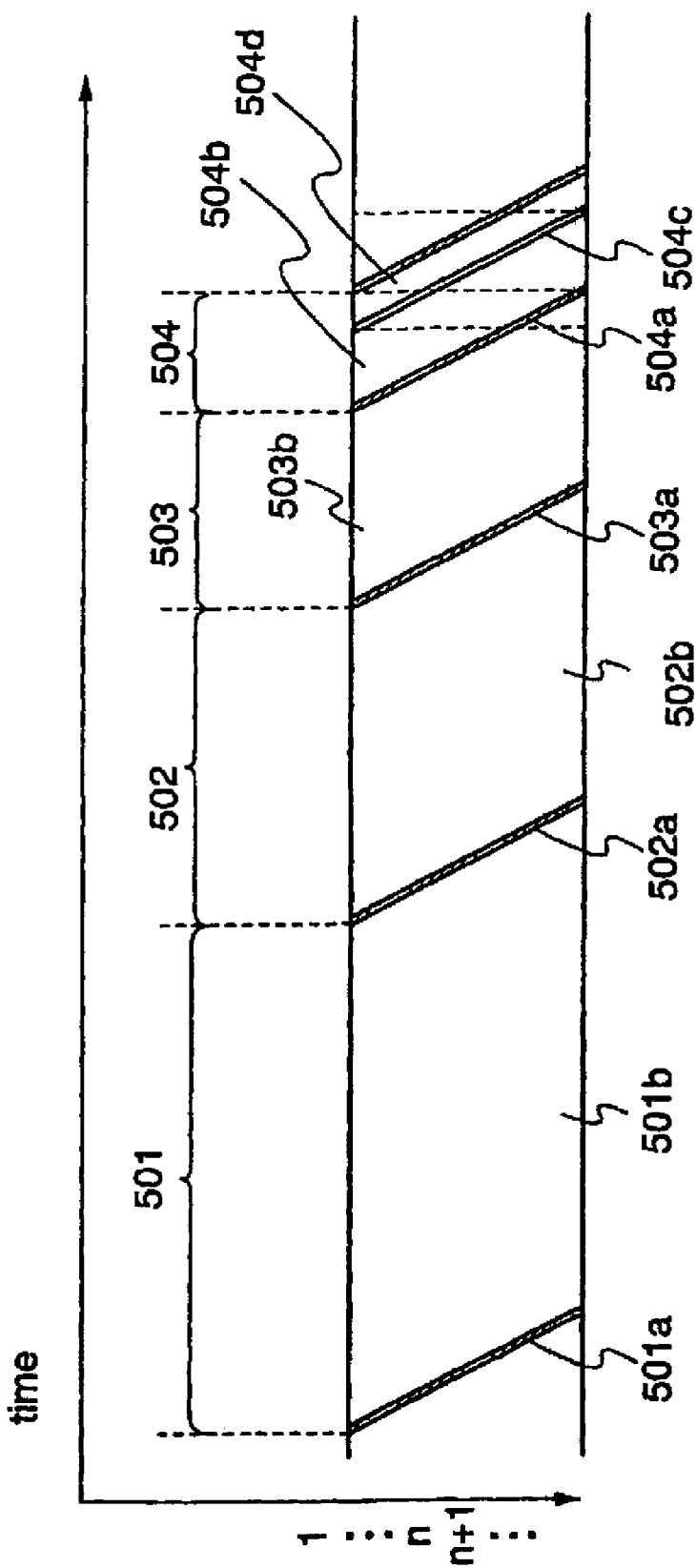
FIG. 6 is an explanatory view of a frame operation of the light-emitting device applied with the present invention.

Then, a driving method is explained. FIG. 6 is an explanatory view of a frame operation with time. In FIG. 6, a horizontal direction represents time, whereas a vertical direction represents the number of scanning steps of the gate signal line.

When displaying an image by using the light-emitting device according to the present invention, rewrite and display operations of a screen are repeated in a display period. The number of rewriting is not especially limited, but preferably approximately 60 times per one second so that a person who views an image does not find flickering of the image. A period in which rewrite and display operations of one image (one frame) are carried out is referred to as one frame period.

As shown in FIG. 6, one frame is time-divided into four sub frames 501, 502, 503, and 504 including writing periods 501*a*, 502*a*, 503*a*, and 504*a*, and retention periods 501*b*, 502*b*, 503*b*, and 504*b*. A light-emitting element that is given signals for emitting light is in an emitting state in the retention period. A ratio of a length of the retention period in each sub frame between the first sub frame 501, the second sub frame 502, the third sub frame 503, and the fourth sub frame 504 is the following: $2^3: 2^2: 2^1: 2^0 = 8: 4: 2: 1$. Accordingly, a 4-bit gray scale can be offered. The number of bits or scales is not limited thereto. For instance, an 8-bit gray scale can be offered by providing eight sub frames.

An operation in one frame is explained. Firstly, a writing operation is carried out from the first line to the last line sequentially in the sub frame 501. Therefore, the starting time of a writing period is different depending on lines. Lines move to the retention period 501*b* in the order of finishing the writing period 501*a*. In the retention period, a light-emitting element that is given signals for emitting light is in an emitting state. Lines move to the next sub frame 502 in the order of finishing the retention period 501*b*, and a writing operation is carried out from the first line to the last line sequentially as is the case with the sub frame 501. Operations as noted above are repeatedly carried out to finish up to the retention period 504*b* of the sub frame 504. When an operation in the sub frame 504 is finished, an operation in the next frame is started. The integration of the time of emitting light in each of the sub frames is an emitting time of each light-emitting element in one frame. By varying the emitting time for each light-emitting element to be variously combined in one pixel, various displaying colors having different luminance and chromaticity can be formed.

In the case that a retention period in the line that finishes writing before finishing the writing up to the last line to be moved to a retention period is intended to be forced into termination as is the case with the sub frame 504, an erasing period 504*c* is preferably provided after the retention period 504*b* to control so that a non-emission state is forcibly formed. The line forced into a non-emission state holds the non-emission state for a certain period (the period is referred to as a non-emission period 504*d*). Upon finishing the writing period of the last line, lines move to the next writing period (or a frame) from the first line. Accordingly, the writing period of the sub frame 504 can be prevented from overlapping a writing period of the next sub frame.

In this embodiment, the sub frames 501 to 504 are arranged in the order of descending retention period; however, the present invention is not limited thereto. For instance, the sub frames 501 to 504 are arranged in the order of ascending retention period. Alternatively, the sub frames 501 to 504 can be arranged randomly. The sub frame may be further divided into a plurality of frames. That is, scanning of the gate signal line can be carried out at a plurality of times during the period of giving the same video signal.

An operation of a circuit illustrated in FIG. 4 is explained in a writing period and an erasing period.

First, an operation in a writing period is explained. In the writing period, the gate signal line 911 at the nth line (n is a natural number) is electrically connected to the gate signal line driver circuit 913 for writing via the switch 918, but disconnected to the gate signal line driver circuit 914 for erasing. The source signal line 912 is electrically connected to the source signal line driver circuit via the switch 920. A signal is input to a gate of the first transistor 901 connected to the gate signal line 911 at the n-th line (n is a natural number), and the first transistor 901 is turned ON. At this time, a video signal is simultaneously input to the source signal line at the first row to the last row. Video signals input from the source signal line 912 at each row are independent to each other. Video signals input from the source signal line 912 are input to the gate electrode of the second transistor 902 via the first transistor 901 connected to each source signal line 912. Signals input to the second transistor 902 controls emission and non-emission of the light-emitting element 903. For instance, in the case that the second transistor 902 is a P-channel type, the light-emitting element 903 emits light by being a Low Level signal input to the gate electrode. On the other hand, in the case that the second transistor 902 is an N-channel type, the light-emitting element 903 emits light by being a High Level signal input to the gate electrode of the second transistor 902.

Then, an operation in an erasing period is explained. In the erasing period, the gate signal line 911 at the n-th line (n is a natural number) is electrically connected to the gate signal line driver circuit 914 for erasing via the switch 919, but disconnected to the gate signal line driver circuit 913 for writing. The source signal line 912 is electrically connected to the power source 916 via the switch 920. A signal is input to the gate electrode of the first transistor 901 connected to the gate signal line 911 at the n-th line, and the first transistor 901 is turned ON. At this time, an erasing signal is simultaneously input to the source signal line at the first row to the last row. The erasing signal input from the source signal line 912 is input to the gate electrode of the second transistor 902 via the first transistor 901 connected to each source signal line. By the signal input to the second transistor 902, current supply from the current supply line 917 to the light-emitting element 903 is stopped. Then, the light-emitting element 903 is forced into a non emission state. In the case that the second transistor 902 is a P-channel type, a light-emitting element 903 does not emit light by being a High Level signal input to a gate electrode of the second transistor 902. On the other hand, in the case that the second transistor 902 is an N-channel type, the light-emitting element 903 does not emit light by being a Low Level signal input to the gate electrode of the second transistor 902.

In the erasing period, a signal for erasing is input by an operation as described above at the n-th line. However, there is the case that the n-th line is in the erasing period and another line (the mth line (m is a natural number) in this instance) is in a writing period. In this instance, it is required that a signal for erasing is input to the n-th line and a signal for writing is input to the m-th line by utilizing a source signal line at the same column. Accordingly, an operation explained as follows is preferably carried out.

Immediately after the light-emitting element 903 at the n-th line is into a non emission state by an operation in the erasing state as explained above, the gate signal line 911 and the gate signal line driver circuit 914 for erasing are made into non-emission states, and the source signal line 912 is connected to the source signal line driver circuit 915 by disconnecting the source signal line 912 from the power source 916 via the switch 920. As well as connecting the source signal line 912 to the source signal line driver circuit 915, the gate signal line is connected to the gate signal line driver circuit 913 for writing. A signal is selectively input to the signal line at the m-th line from the gate signal line driver circuit 913 for writing, and the first transistor is turned ON, simultaneously, a signal for writing is input to the source signal line at the first column to the last column from the source signal line driver circuit 915. By the signal, the light-emitting element at the m-th line becomes in an emission state or a non-emission state.

Immediately after finishing the writing period of the m-th line as noted above, lines move to an erasing period at the (n+1)th line. Hence, the gate signal line 911 and the gate signal driver circuit 913 for writing are disconnected, simultaneously; a source signal line 912 and the power source 916 are connected by disconnecting the source signal line 912 from the source signal line driver circuit 915 via switch 920. Further, the gate signal line 911 and the gate signal line driver circuit 913 for writing are disconnected, simultaneously; the gate signal line 911 is connected to the gate signal line driver circuit 914 for erasing. A signal is selectively input to the gate signal line at the (n+1)-th line from the gate signal line driver circuit 914 for erasing, and the first transistor 901 is turned ON, simultaneously, an erasing signal is input from the power source 916. As noted above, immediately after finishing an erasing period at the (n+1)-th line, lines move to an writing period at the m-th line. Hereinafter, an erasing period and a writing period may be carried out repeatedly to operate up to an erasing period at the last line.

In this embodiment, a mode in which the writing period at the mth line, but not exclusively, is provided between an erasing period at the n-th line and the erasing period at the (n+1)-th line is explained. The writing period at the mth line can be provided between an erasing period at the (n−1)-th line and an erasing period at the n-th line.

In this embodiment, in the case that the non emission period 504d is provided as with the sub frame 504, an operation of disconnecting the gate signal line driver circuit 914 for erasing and a certain gate signal line and an operation of connecting the gate signal line driver circuit 913 for writing to another gate signal line are simultaneously and repeatedly carried out. Such the operations can be carried out in the frame that is not provided with a non-emission period.

Embodiment 4

One embodiment of a cross-sectional view of a light-emitting device including the light-emitting element according to the present invention is explained with reference to FIGS. 7A to 7C.

Figure 7A:
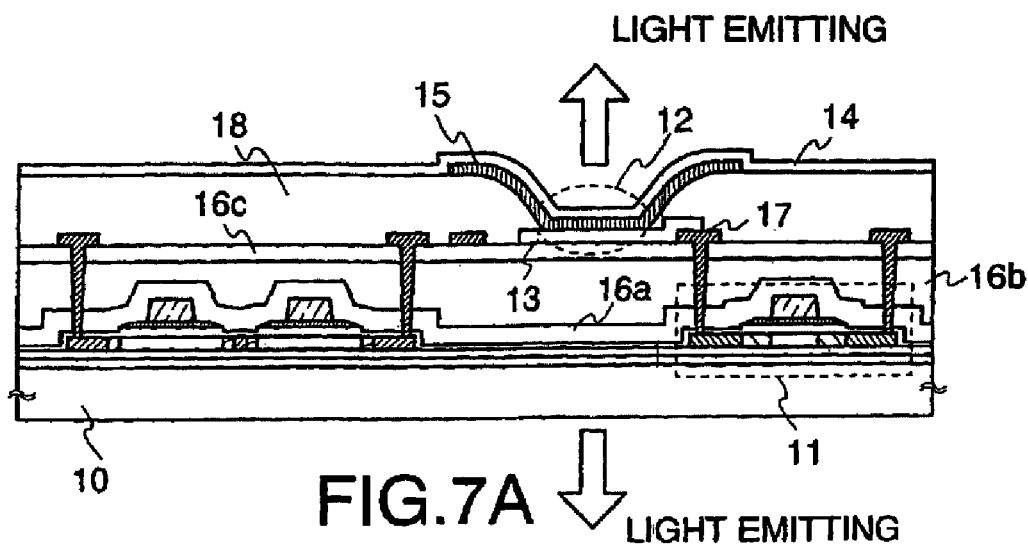
FIGS. 7A to 7C are cross-sectional views of the light-emitting device applied with the present invention.
Figure 7B:
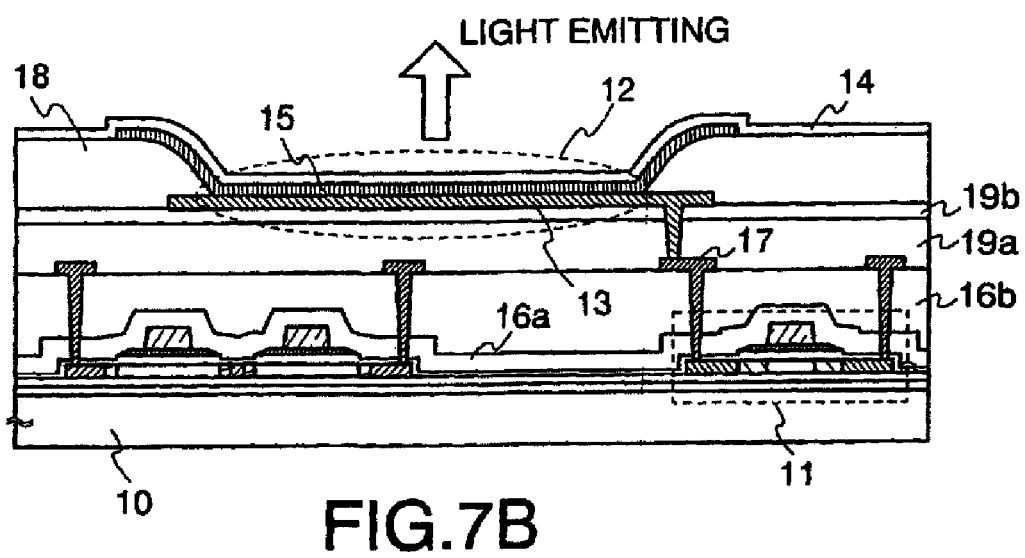
Figure 7C:
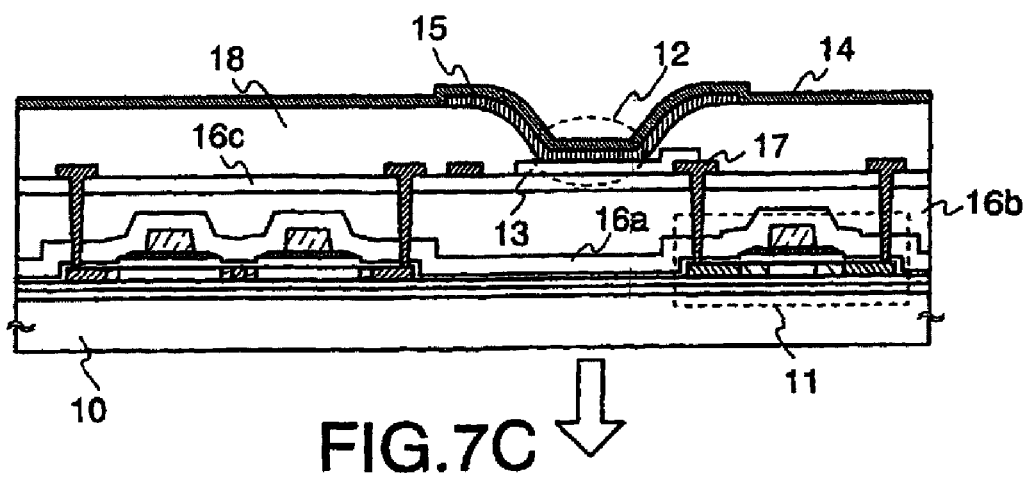

In FIGS. 7A to 7C, a portion surrounded by dotted box line denotes a transistor 11 provided to drive a light-emitting element 12 according to the present invention. The light-emitting element 12 is a light-emitting element according to the present invention that has a light-emitting layer 15 interposed between a first electrode 13 and a second electrode 14. The drain of the transistor 11 is electrically connected to the first electrode 13 by a wiring 17 that penetrates into a first interlayer insulating films 16a, 16b, and 16c. Further, the light-emitting element 12 is separated from another light-emitting element provided adjacently with a bank layer 18. A light-emitting device according to the present invention having such the structure is provided over a substrate 10 in this embodiment.

Each transistor illustrated in FIGS. 7A to 7C is a top gate type in which a gate electrode is provided to the side opposite to the substrate so as to interpose a semiconductor layer between the gate electrode and the substrate. The structure of the transistor 11 is not especially limited. For instance, the transistor 11 may be a bottom gate type. In the case of the bottom gate type, the transistor may have a channel protective type in which a protective film is formed over a part of a semiconductor layer that forms a channel region, or a channel etch type in which the semiconductor layer that forms a channel region is partly formed to have a concave portion.

The semiconductor layer that constitutes the transistor 11 may be either a crystalline semiconductor layer or an amorphous semiconductor layer. Alternatively, a semiamorphous semiconductor layer can be used.

The semiamorphous semiconductor is explained as follows: the semiamorphous semiconductor has an intermediate structure between an amorphous structure and a crystalline structure (including single crystals and poly crystals). The semiamorphous semiconductor has a stable third state with respect to free energy, and a crystalline region having a short-range order and lattice distortion. At least a part of the semiamorphous semiconductor film includes crystal grains with grain diameters of from 0.5 to 20 nm. A raman spectrum peak derived from L-O phonon is shifted to a lower wave number than 520 cm$^{-1}$. By X-ray diffraction, diffraction peaks (111), (220) that may be derived from a Si crystalline lattice are observed. Hydrogen or halogen of 1 atomic % or more is contained in the semiamorphous semiconductor as neutralizer for terminating dangling bond. Such the semiamorphous semiconductor is referred to as what is called micro crystal semiconductor. The semiamorphous semiconductor is formed using a silicide gas formed by glow discharge decomposition (plasma CVD). As the silicide gas, $Si_2H_6$, $SiH_2Cl_2$, $SiHCl_3$, $SiCl_4$, $SiF_4$, or the like in addition to $SiH_4$ can be used. The silicide gas can be diluted by $H_2$, or the $H_2$ and one or a plurality of rare gas elements selected from the group consisting of He, Ar, Kr, and Ne. The dilution rate is in the range of from 2 to 1000 times. An applied voltage is in the range of from 0.1 to 133 Pa. A power source frequency is in the range of from 1 to 120 MHz, preferably, 13 to 60 MHz. A substrate heating temperature is at most 300° C., preferably, from 100 to 250° C. As impurity elements in the film, atmospheric constituents such as oxygen, nitrogen, carbon, and the like have preferably density of $1 \times 10^{20}/cm^3$ or less, especially, oxygen density is $5 \times 10^{19}/cm^3$ or less, preferably, $1 \times 10^{19}/cm^3$ or less. A TFT (thin film transistor) including the semiamorphous semiconductor has mobility of approximately from 1 to 10 $cm^2/Vsec$.

As a specific example of a crystalline semiconductor layer, a semiconductor layer formed by single crystalline silicon, polycrystalline silicon, silicon germanium, or the like can be nominated. These semiconductor layers may be formed by laser crystallization, or crystallization by a solid phase growth method using nickel or the like.

In the case that a semiconductor layer is formed by an amorphous material, for example, amorphous silicon; a light-emitting device has preferably a circuit composed of the transistor 11 and the other transistors (for composing a circuit for driving a light-emitting element), each of which is formed by an N-channel type transistor. In the case that a semiconductor layer is formed by a material other than the amorphous material, a light-emitting device may have a circuit composed of either an N-channel type transistor or a P-channel type transistor; or a light-emitting device may have a circuit composed of both of the N-channel type transistor and the P-channel type transistor.

The first interlayer insulating films 16a to 16c may be formed by a multiple layers as shown in FIGS. 7A to 7C or a single layer. The interlayer insulating film 16a is made from an inorganic material such as silicon oxide or silicon nitride, the interlayer insulating film 16b is made from acrylic, siloxane (Siloxane is composed of a skeleton formed by the bond of silicon (Si) and oxygen (O), in which an organic group containing at least hydrogen (such as an alkyl group or aromatic hydrocarbon) is included as a substituent. Alternatively, a fluoro group may be used as the substituent. Further alternatively, a fluoro group and an organic group containing at least hydrogen may be used as the substituent.), silicon oxide capable of being coated as a film, or the like, and the interlayer insulating film 16c is made from a silicon nitride film containing argon (Ar). A material that constitutes each layer is not especially limited, a material other than the foregoing materials can be used. A layer made from a material other than the foregoing materials can be stacked. As noted above, the first interlayer insulating films 16a to 16c can be formed by both of an inorganic material and an organic material or either of the inorganic material or the organic material.

The bank layer 18 is preferably formed to have an edge portion having the radius of curvature that varies continuously. The bank layer 18 is made from acrylic, siloxane, resist, silicon oxide, or the like. The bank layer 18 may be formed by either of an inorganic film or an organic film, or both of the inorganic film and the organic film.

In FIGS. 7A and 7C, only the first interlayer insulating films 16a to 16c are formed between the transistor 11 and the light-emitting element 12. Alternatively, not only the first interlayer insulating films 16a and 16b, but also second interlayer insulating films 19a and 19b can be formed between the transistor 11 and the light-emitting element 12. In the light-emitting device shown in FIG. 7B, the first electrode 13 penetrates the second interlayer insulating films 19a and 19b to connect to the wiring 17.

The second interlayer insulating films 19a and 19b may be formed by a multiple layers as with the first interlayer insulating films 16a to 16c or a single layer. The second interlayer insulating film 19a is made from acrylic, siloxane, silicon oxide capable of being coated as a film, or the like, and the second interlayer insulating film 19b is formed by a silicon nitride film containing argon (Ar). A material that constitutes each layer is not especially limited, a material other than the foregoing materials can be used. A layer made from a material other than the foregoing materials can be stacked. As noted above, the second interlayer insulating films 19a and 19b can be formed by both of an inorganic material and an organic material or either of the inorganic material or the organic material.

In the case that both of the first electrode 13 and the second electrode 14 are made from a material having light transmitting property in the light-emitting element 12, light can be extracted from both of the first electrode 13 side and the second electrode 14 side as indicated by outline arrow in FIG. 7A. In the case that only the second electrode 14 is made from a material having light transmitting property in the light-emitting element 12, light can be extracted from only the second electrode 14 side as indicated by outline arrow in FIG. 7B. In this instance, the first electrode 13 is preferably formed by a material having high reflectivity or a film made from a material having high reflectivity (reflective film) is preferably provided at the underside of the first electrode 13. In the case that only the first electrode 13 is made from a material having light transmitting property, light can be extracted from only the first electrode 13 side as indicated by outline arrow in FIG. 7C. In this instance, the second electrode 14 is preferably made from a material having high reflectivity, or a reflective film is preferably formed at the upper side of the second electrode 14.

In the light-emitting element 12, the first electrode 13 may serve as an anode, whereas the second electrode 14 may serve as a cathode, alternatively, the first electrode 13 may serve as a cathode, whereas the second electrode 14 may serve as an anode. In the first case, the transistor 11 is a P-channel type transistor. In the latter case, the transistor 11 is an N-channel transistor.

Embodiment 5

An electric appliance which can perform favorable display for a long time or an electronic apparatus which can favorably light for a long time can be obtained by applying a light emitting device according to the present invention.

Specific examples of the electric appliances having the light emitting device according to the present invention are shown in FIGS. 8A to 8C.

FIG. 8A shows a laptop computer including a main body 5521, a housing 5522, a display portion 5523, a keyboard 5524 and the like which is manufactured by applying the present invention. The laptop computer is completed by incorporating the light emitting device having light emitting element of the present invention as the display portion 5523.

FIG. 8B shows a mobile phone including a main body 5552, a display portion 5551, a voice output portion 5554, a voice input portion 5555, operating keys 5556, 5557, an antenna 5553 and the like which is manufactured by applying the present invention. The mobile phone is completed by incorporating the light emitting device having the light emitting element according to the present invention as the display portion 5551.

FIG. 8C shows a TV broadcast receiver including a display portion 5531, a housing 5532, a speaker 5533 and the like which is manufactured by applying the present invention. The TV broadcast receiver is completed by incorporating the light emitting device having the light emitting element of the present invention as the display portion 5531.

As described above, the light emitting device of the present invention is extremely suitable as a display portion of various electric appliances.

In this embodiment, in addition to those electric appliances described above, the light emitting device having the light emitting element of the present invention may be mounted to a car navigation system, a lightning apparatus or the like.

EXAMPLE 1

SYNTHESIS EXAMPLE 1

A synthesis method of a benzidine derivative illustrated in structural formula (2) is explained.

Step 1

Synthesis of 2-bromo-spiro-9,9'-bifluorene

A 100 ml three neck distilling flask was charged with magnesium (1.26 g, 0.052 mol). Vacuum was formed in a system. The magnesium was heated to stir for 30 minutes to be activated. After cooling to room temperature, nitrogen gas stream was formed in the system. Then, 5 ml diethyl ether and a few drops of dibromoethane were added. And then, 2-bromobiphenyl (11.65 g, 0.050 mol) dissolved in 15 ml diethyl ether was slowly dropped. After dropping, the reaction was refluxed for 3 hours to be a Grignard reagent. A 200 ml three neck distilling flask was charged with 2-bromofluorenone (11.7 g, 0.045 mol) and 40 ml diethyl ether. The synthesized Grignard reagent was slowly dropped to the reacted solution. After the dropping, the solution was refluxed for 2 hours and stirred at room temperature overnight. After reaction, the reacted solution was washed with saturated ammonium chloride solution twice, and a water layer was extracted with ethyl acetate twice and washed with saturated salt solution twice with an organic layer. After drying with magnesium sulfite, the reacted solution was suctioned and filtrated, and condensed to give 18.76 g 9-(2-biphenylyl)-2-bromo-9-fluorenol in a solid state in a yield of 90%.

A 200 three neck distilling flask was charged with the synthesized 9-(2-biphenylyl)-2-bromo-9-fluorenol (18.76 g, 0.045 mol), 100 ml glacial acetic acid, and a few drops of concentrated hydrochloric acid to be refluxed for 2 hours. After reaction, deposits were collected by saturation and filtration, and filtrated and washed with saturated sodium hydrogencarbonate and water. Obtained brown solid matter was recrystallized from ethanol to give light brown powdery solid matter weighed 10.24 g in a yield of 57%. The $^1$H-NMR spectrum of the light brown powdery solid matter was obtained to confirm that it was 2-bromo-spiro-9,9'-bifluorene, and the result was as follows:

$^1$H-NMR (300 MHz, CDCl$_3$) δppm: 7.86-7.79 (m, 3H), 7.70 (d, 1H, J=8.4 Hz), 7.47-7.50 (m, 1H), 7.41-7.34 (m, 3H), 7.12 (t, 3H, J=7.7 Hz), 6.85 (d, 1H, J=2.1 Hz), 6.74-6.70 (m, 3H)

A synthesis scheme (b-1) of the synthesis method explained above is represented as follows:

(b-1)

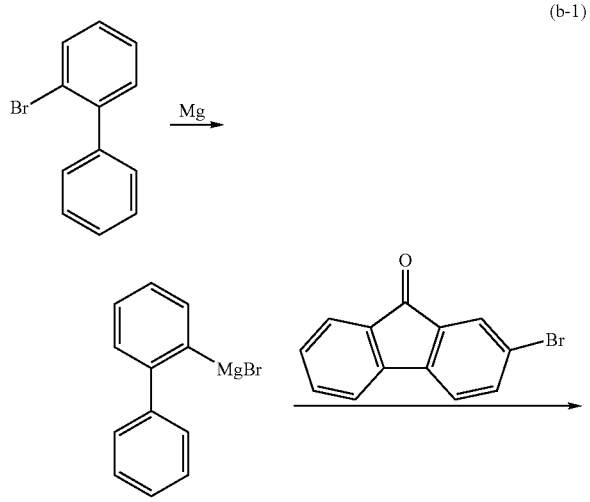

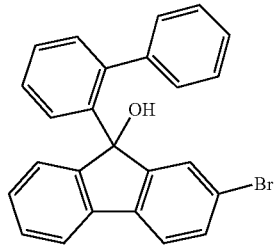

[Step 2]

Synthesis N,N'-bis(spiro-9,9'-bifluorene-2-yl)-N,N'-diphenylbenzidine (abbreviated as BSPB)

A 100 ml three neck distilling flask was charged with N,N'-diphenylbenzidine (1.00 g, 0.0030 mol), 2-bromo-spiro-9,9'-bifluorene (2.49 g, 0.0062 mol) synthesized by a synthesis method explained in Step 1, Bis(dibenzylideneacetone)palladium (170 mg, 0.30 mmol), and tert-butoxy sodium (1.08 g, 0.011 mol). After forming nitrogen gas stream in a system, 20 ml dehydrated toluene and 0.6 ml tri-tert-butylphosphine 10% hexane solution were added and stirred at 80° C. for 6 hours. After the reaction, the reaction solution was cooled to room temperature, and water was added thereto to collect deposited solid matter by suction filtration. Then, the solid matter was washed with dichloromethane. Obtained white solid matter was purified by alumina column chromatography (chloroform) and recrystallized from dichloromethane to give white powered solid matter (2.66 g) in a yield of 93%.

Figure 15:
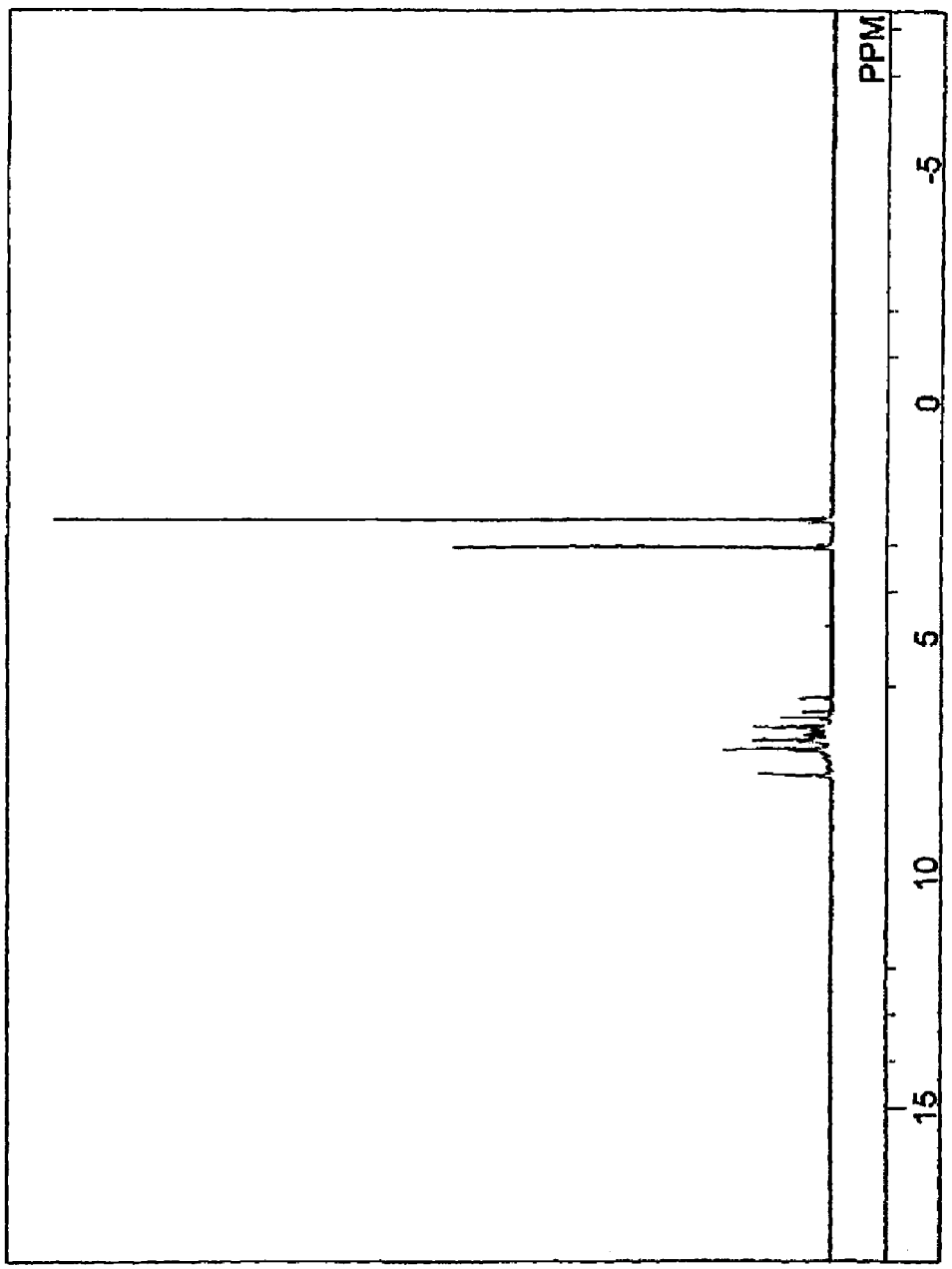
FIG. 15 is a view for showing a $^1$H-NMR spectrum result of a white powdered solid matter synthesized according to Step 2 of Synthesis Example 1.

The $^1$H-NMR spectrum of the obtained white powered solid matter was obtained to confirm that the product was a benzidine derivative as represented by structural formula (2). FIG. 15 shows the $^1$H-NMR chart. The $^1$H-NMR spectrum result was as follows:

$^1$H-NMR (300 MHz, DMSO-d$_6$) δ ppm: 7.93-7.89 (m, 8H), 7.39-7.33 (m, 10H), 7.19-7.14 (m, 8H), 7.09-6.96 (m, 6H), 6.89-6.84 (m, 8H), 6.69 (d, 4H, J=7.5 Hz), 6.54 (d, 2H, J=7.8H), 6.25 (d, 2H, J=2.4 Hz)

As noted above, the compound according to the present invention can be synthesized by a coupling reaction of N,N'-diphenylbenzidine and 2-bromo-spiro-9,9'-bifluorene. A synthesis scheme (b-2) of the synthesis method explained above is represented as follows:

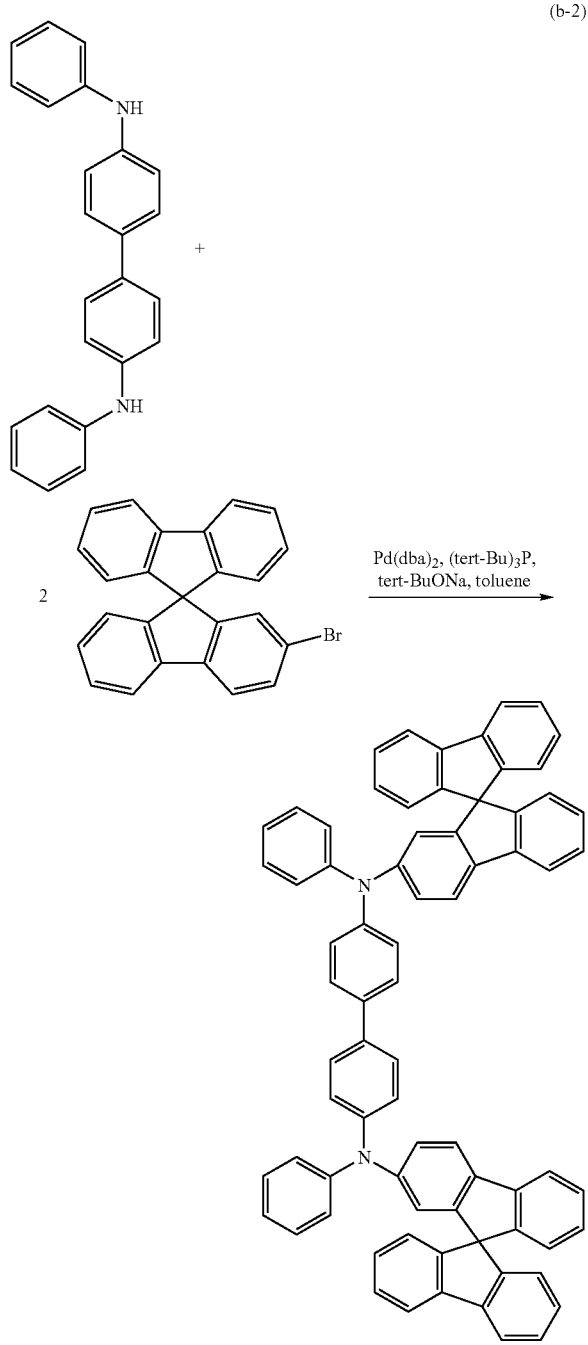

tical axis represents heat flow (upward direction represents endotherm) (mW). From the measurement result, the glass-transition temperature of the obtained compound was 172° C., and the crystallization temperature of the obtained compound was 268° C. Further, the melting point was from 323 to 324° C. from the intersection of a tangential line at 312° C. with a tangential line at from 327 to 328° C. The obtained compound had high glass-transition temperature of 172° C. and favorable heat resistance. The obtained compound was a substance that is difficult to be crystallized from the fact that the peak in FIG. 9 that indicates crystallization of the obtained compound was broad.

Figure 10:
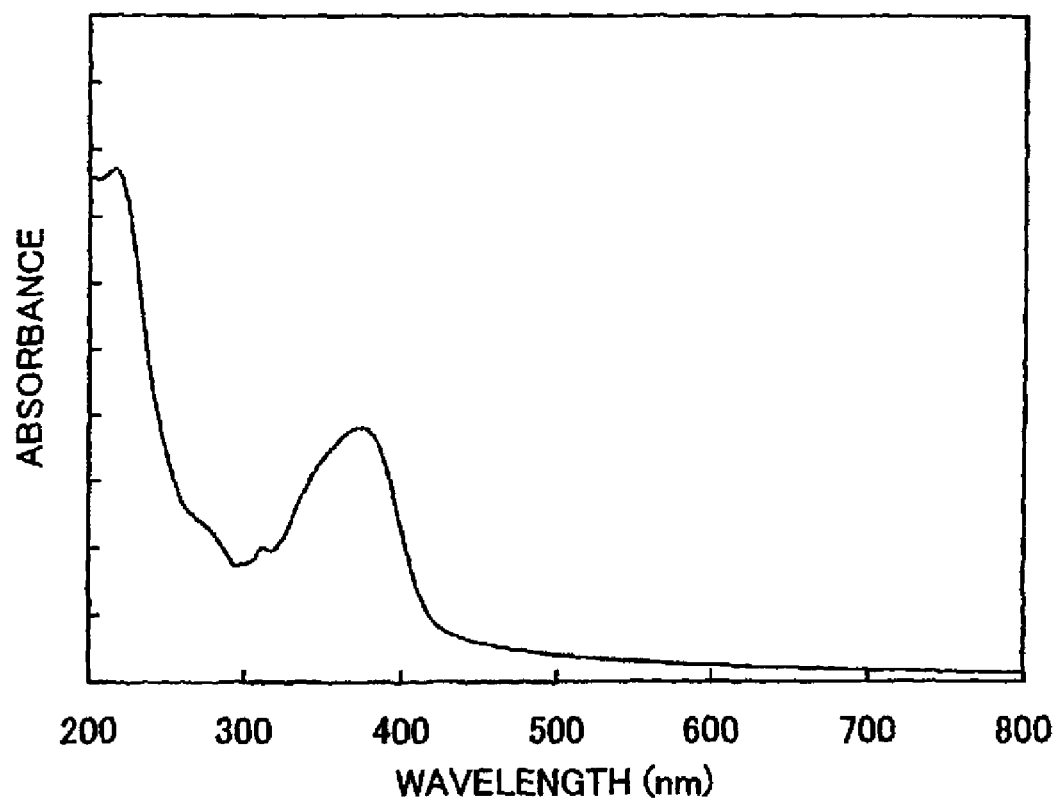
FIG. 10 is an absorption spectrum of the benzidine derivative according to the present invention.
Figure 11:
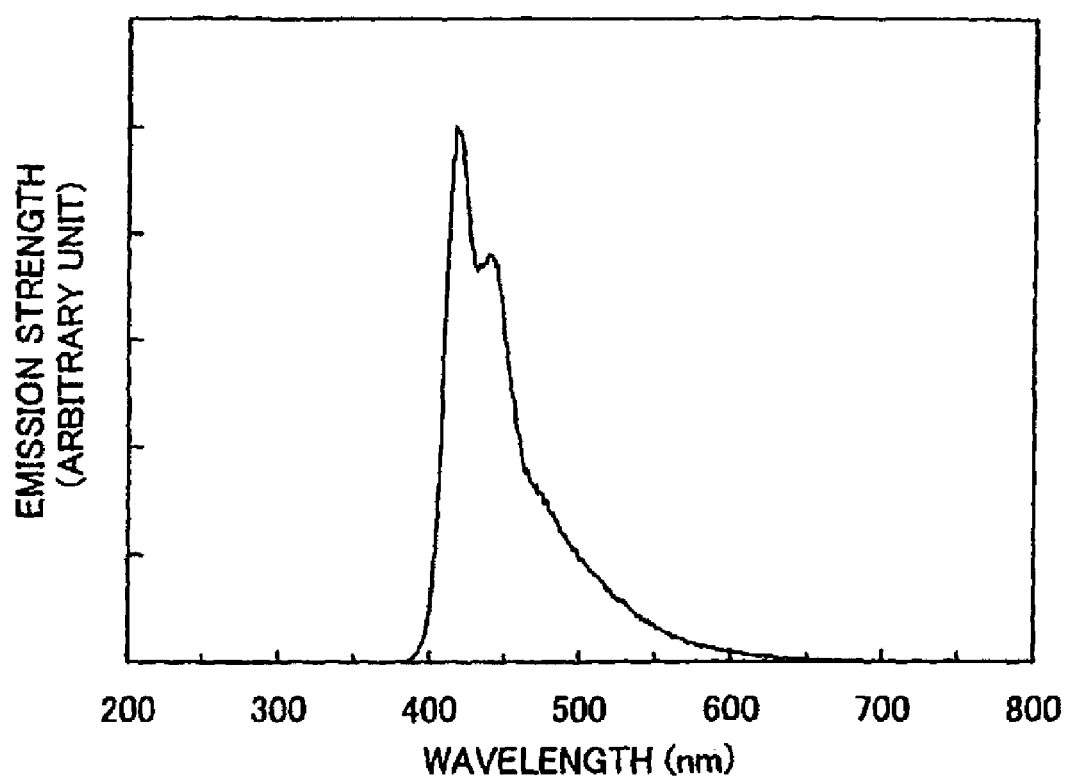
FIG. 11 is an emission spectrum of the benzidine derivative according to the present invention.

The obtained compound was deposited by vapor deposition. The ionization potential of −5.3 eV of the deposited compound in a thin film state was obtained by the measurement by photoelectron spectrometer (AC-2) (RIKEN KEIKI Co., Ltd). Further, the LUMO level of −2.5 eV was obtained by measuring the absorption spectrum of the deposited compound in a thin film state by UV/VIS spectrometer (V-550) (JASCO International Co., Ltd.) considering that a wavelength of an absorption edge at a long wavelength side of the absorption spectrum is an energy gap. FIG. 10 shows the absorption spectrum of the obtained compound in a thin film state. In FIG. 10, a horizontal axis represents absorbance (no unit), whereas a vertical axis represents a wavelength (nm). FIG. 11 shows an emission spectrum of the obtained compound in a thin film state. In FIG. 11, a horizontal axis represents an emission strength (arbitrary unit), whereas a vertical axis represents a wavelength (nm).

The obtained compound (4.74 g) was sublimed and purified under the condition of 14 Pa and 350° C. for 24 hours to collect 3.49 g compound in a yield of 74%.

EXAMPLE 2

Figure 2:
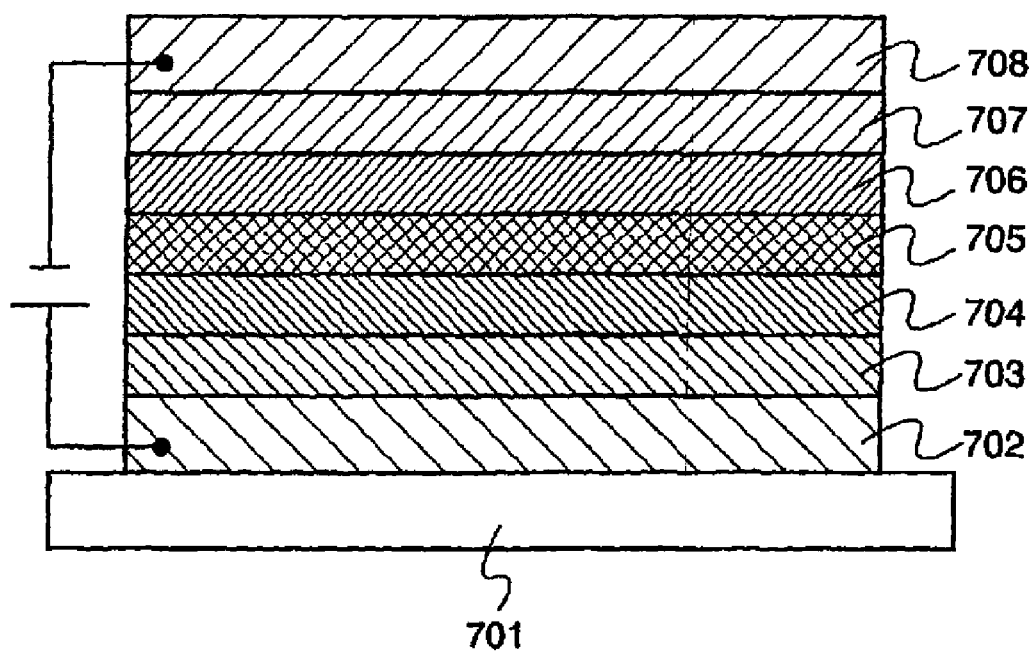
FIG. 2 is an explanatory view of the light-emitting element according to the present invention.

A light-emitting element manufactured by using the compound (hereinafter, BSPB) having glass-transition temperature of 172° C. obtained by the synthesis according to Step 2 in Synthesis example 1 is explained with reference to FIG. 2.

Indium tin oxide containing silicon was deposited over a glass substrate 701 by a sputtering method to form a first electrode 702 with a thickness of 110 nm.

Then, DNTPD was deposited over the first electrode 702 by a vacuum deposition method to form a first layer 703 made from the DNTPD with a thickness of 50 nm.

And then, BSPB was deposited over the first layer 703 made from the DNTPD by a vacuum deposition method to form a second layer 704 made from the BSPB with a thickness of 10 nm.

Alq$_3$ and coumarin 6 were deposited over the second layer 704 made from BSPB by a co-evaporation method to form a third layer 705 containing the Alq$_3$ and the coumarin 6. The third layer 705 contains the coumarin 6 of 0.5 percent by mass to the Alq$_3$. Accordingly, the coumarin 6 was in the state of being scattered in the Alq$_3$. The third layer 705 was formed to have a thickness of 37.5 nm. The co-evaporation method refers to a vapor deposition method by which a material is deposited from a plurality of evaporation sources simultaneously.

Alq$_3$ was deposited over the third layer 705 containing Alq$_3$ and coumarin 6 by a vacuum deposition method to form a fourth layer 706 made from the Alq$_3$ with a thickness of 37.5 nm.

Calcium fluoride was deposited over the fourth layer 706 made from Alq$_3$ by a vacuum deposition method to form a fifth layer 707 made from the calcium fluoride with a thickness of 1 nm.

Figure 9:
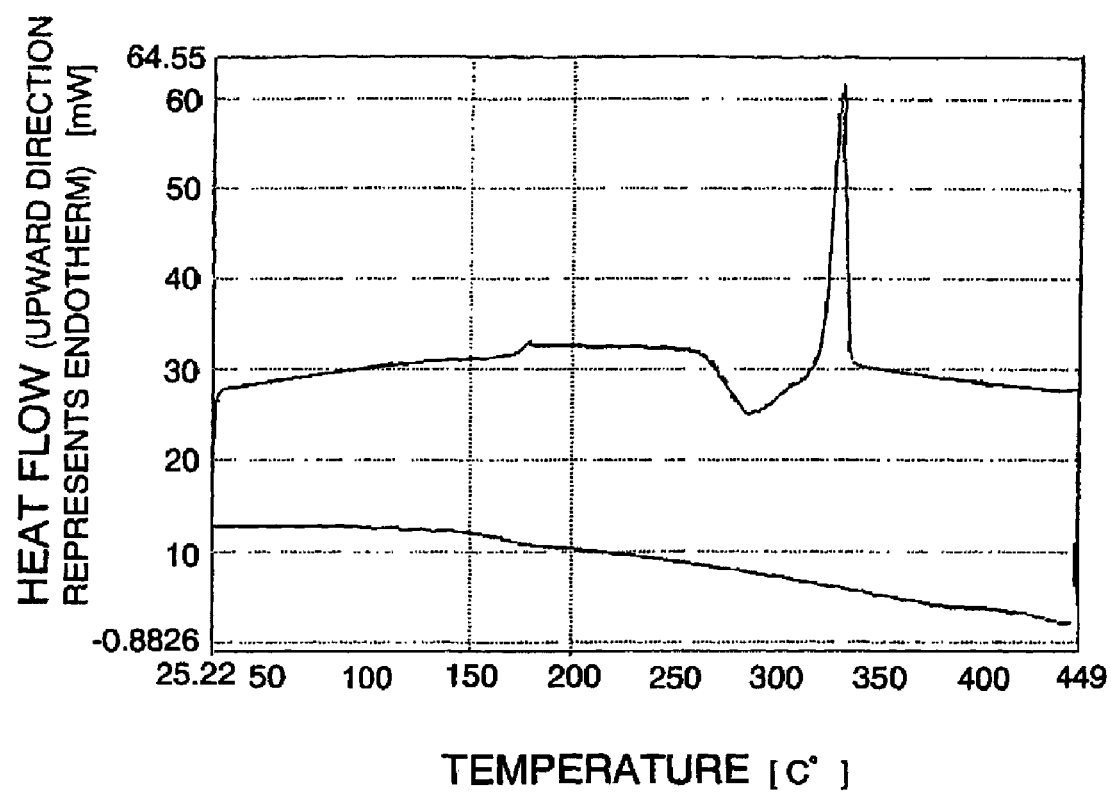
FIG. 9 is a view for showing measurement results of differential scanning calorimetry of the benzidine derivative according to the present invention.

The glass-transition temperature, crystallization temperature, and melting point of the obtained compound were obtained by Differential Scanning Calorimetry (DSC) manufactured by PerkinElmer, Inc. under model number Pyrisl DSC. The measurement by the DSC was carried out in the following procedure, that is, a sample (obtained compound) was heated to 450° C. at programming rate of 40° C./minutes, the sample was cooled at programming rate of 40° C./minutes to be a glass state, and the glass state sample was heated at programming rate of 10° C./minutes. Hence, the measurement result was obtained as shown in FIG. 9. In FIG. 9, a horizontal axis represents temperature (° C.), whereas a ver- Aluminum was deposited over the fifth layer 707 made form the calcium fluoride by a vacuum deposition method to form a second electrode 708.

When current is passed through the first electrode 702 and the second electrode 708 by applying voltage thereto in a light-emitting element manufactured as noted above, the coumarin 6 emits light. In this case, the first electrode 702 serves as an anode, whereas the second electrode 708 serves as a cathode. Further, the layer 703 made from the DNTPD serves as a hole injecting layer, the layer 704 made from the BSPB serves as a hole transporting layer, the layer 705 containing the Alq$_3$ and the coumarin 6 serves as a light-emitting layer, the layer 706 made from the Alq$_3$ serves as an electron transporting layer, and the layer 707 made from the fluoride calcium serves as an electron injecting layer in the light-emitting element.

Figure 12:
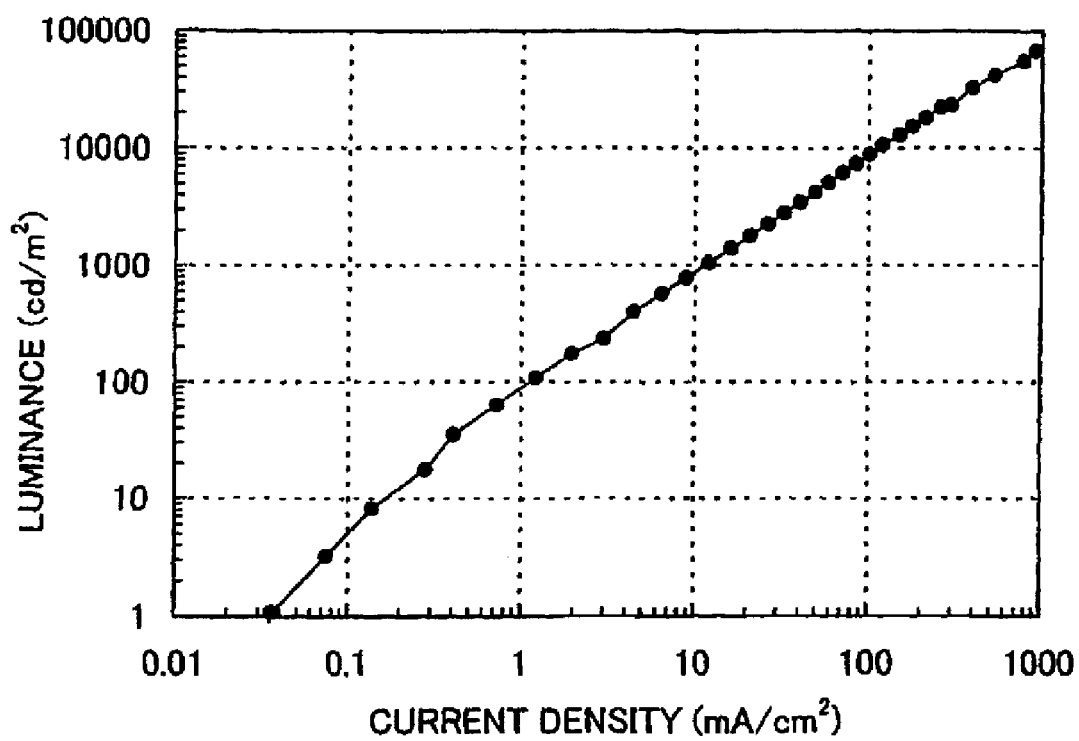
FIG. 12 is a view for showing current density-luminance characteristics of a light-emitting element using the benzidine derivative according to the present invention.
Figure 13:
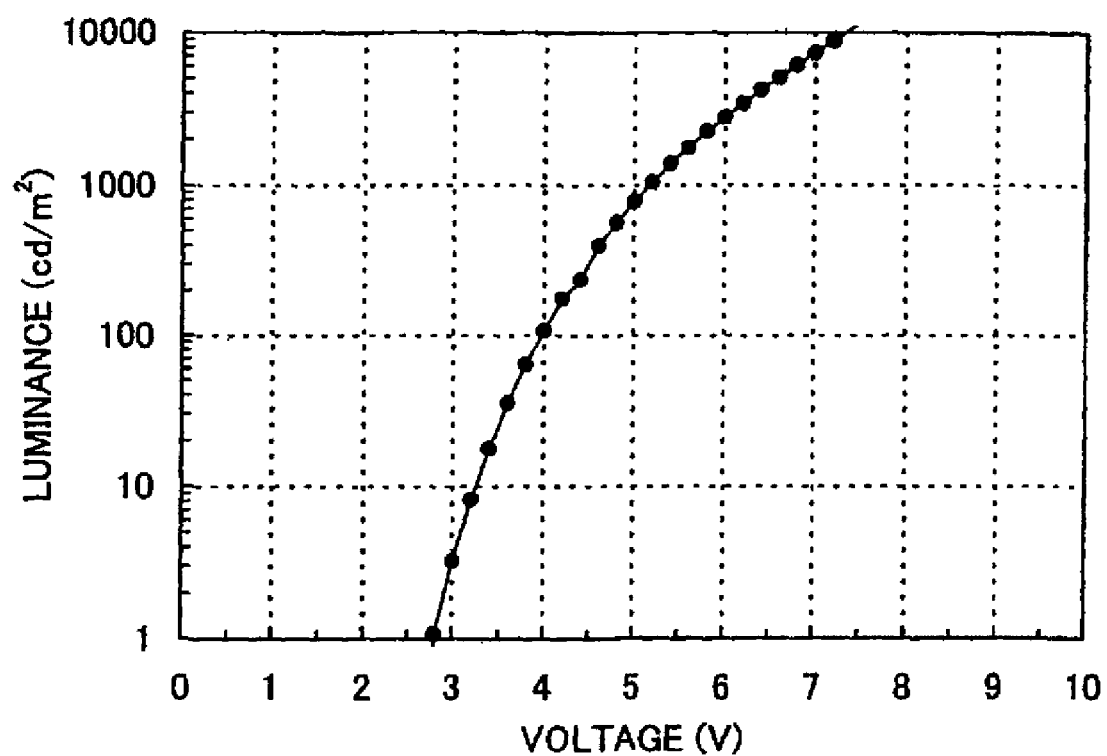
FIG. 13 is a view for showing voltage-luminance characteristics of the light-emitting element using the benzidine derivative according to the present invention.
Figure 14:
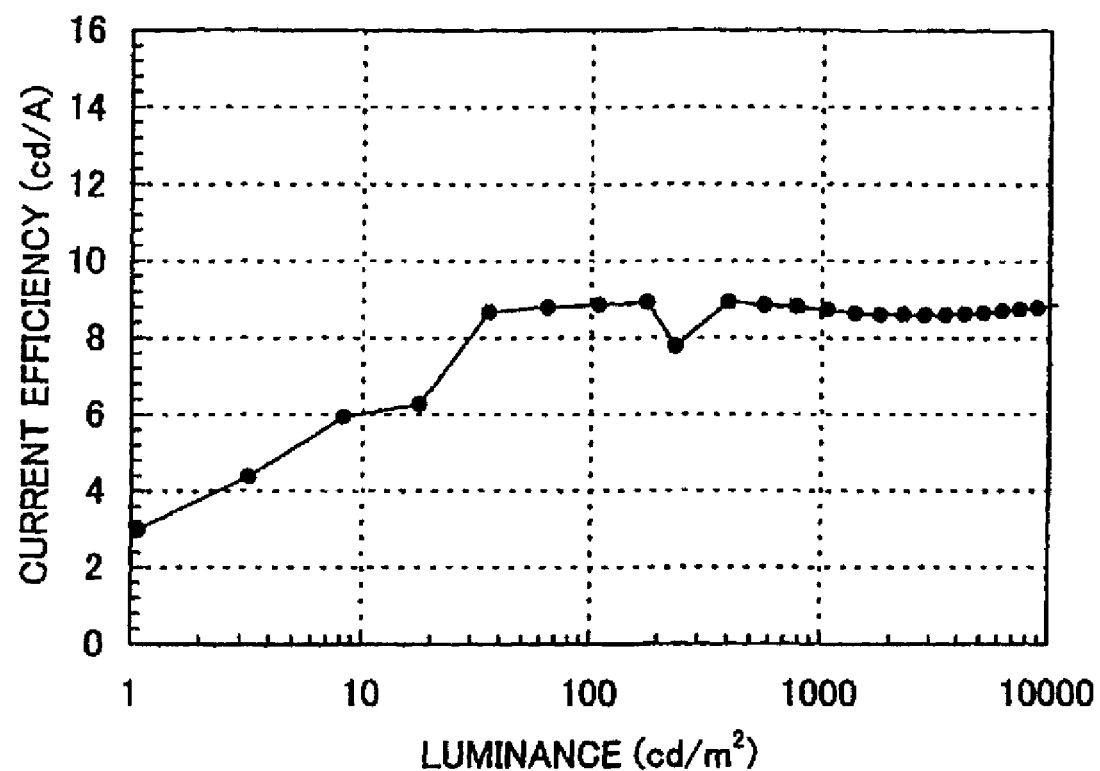
FIG. 14 is a view for showing luminance-current efficiency characteristics of the light-emitting element using the benzidine derivative according to the present invention.

FIG. 12 shows current density-luminance characteristics of the light-emitting element according to this example. FIG. 13 shows voltage-luminance characteristics thereof. FIG. 14 shows luminance-current efficiency characteristics thereof. In FIG. 12, a horizontal axis represents current density, whereas a vertical axis represents luminance. In FIG. 13, a horizontal axis represents voltage, whereas a vertical axis represents luminance. In FIG. 14, a horizontal axis represents luminance, whereas a vertical axis represents current efficiency.

LIST OF REFERENCE NUMERALS

101: first electrode
102: second electrode
111: hole injecting layer
112: hole transporting layer
113: light-emitting layer
114: electron transporting layer
115: electron injecting layer
701: substrate
702: first electrode
703: first layer
704: second layer
705: third layer
706: fourth layer
707: fifth layer
708: second electrode
6500: substrate
6503: FPC
6504: printed wiring board (PWB)
6511: pixel portion
6512: source signal line driver circuit
6513: gate signal line driver circuit for writing
6514: gate signal line driver circuit for erasing
901: first transistor
902: second transistor
903: light-emitting element
911: gate signal line
912: source signal line
913: gate signal line driver circuit for writing
914: gate signal line driver circuit for erasing
915: source signal line driver circuit
916: vower source
917: current supply line
918: switch
919: switch
920: switch
1001: first transistor
1002: second transistor
1003: gate signal line
1004: source signal line
1005: current supply line
1006: electrode
501: sub frame
502: sub frame
503: sub frame
504: sub frame
501*a*: writing period
501*b*: retention period
502*a*: writing period
502*b*: retention period
503*a*: writing period
503*b*: retention period
504*a*: writing period
504*b*: retention period
504*c*: erasing period
504*d*: non-emission period
10: substrate
11: transistor
12: light-emitting element
13: first electrode
14: second electrode
15: light-emitting layer
16: first interlayer insulating films
16*a*: first interlayer insulating film
16*b*: first interlayer insulating film
16*c*: first interlayer insulating film
17: wiring
18: bank layer
19: second interlayer insulating films
19*a*: second interlayer insulating film
19*b*: second interlayer insulating film
5521: main body
5522: housing
5523: display portion
5524: keyboard
5551: display portion
5552: main body
5553: antenna
5554: voice output portion
5555: voice input portion
5556: operating key
5531: display portion
5532: housing
5533: speaker An emission spectrum of the light-emitting element according to this example has a peak at 510 nm with the CIE chromaticity coordinates x=0.25, y=0.66.

Hence, the light-emitting element according to this example can obtain good light emission derived from the coumarin 6. It is considered that this arises from the fact that excitation energy does not move from the layer 705 serving as a light-emitting layer to a layer made from the benzidine derivative according to the present invention, and the layer made from the benzidine derivative serves well as a hole transporting layer. Therefore, the benzidine derivative according to the present invention is suitable for a hole transporting material.

The invention claimed is:

1. A benzidine derivative represented by a general formula (1):

(1)

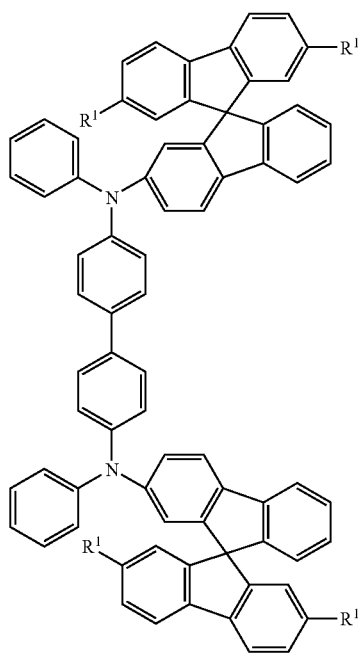

wherein R¹ is hydrogen or an alkyl group having carbon atoms 1-4.

2. A benzidine derivative represented by a structural formula (2):

(2)

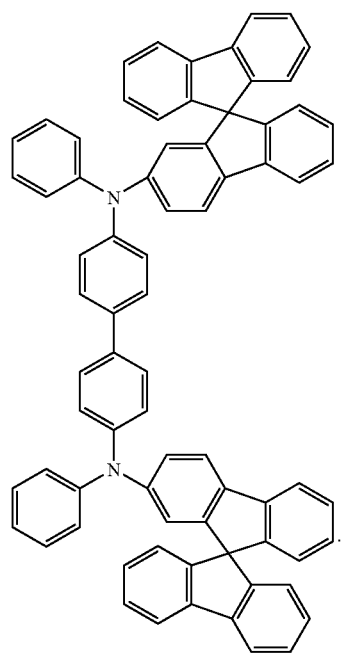

3. A compound obtained by a coupling reaction of N,N'-diphenylbenzidine with 2-bromo-spiro-9,9'-bifluorene,
wherein the compound has a melting point of from 323 to 324° C.

4. A hole transporting material containing a benzidine derivative represented by a general formula (1):

(1)

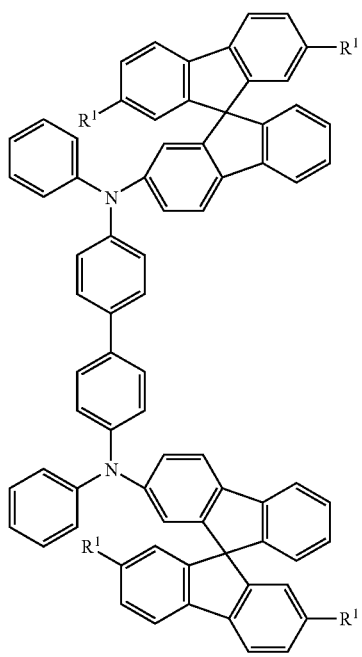

wherein R¹ is hydrogen or an alkyl group having carbon atoms 1-4.

5. A hole transporting material containing a benzidine derivative represented by a structural formula (2):

(2)

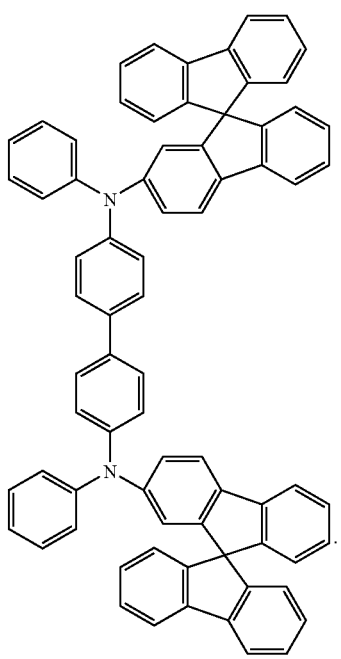

6. A hole transporting material containing a compound obtained by a coupling reaction of N,N'-diphenylbenzidine with 2-bromo-spiro-9,9'-bifluorene,
wherein the compound has a melting point of from 323 to 324° C.

7. A light emitting device comprising a light emitting element,
wherein the light emitting element comprises a layer including a beuzidine derivative represented by a general formula (1) between a pair of electrodes

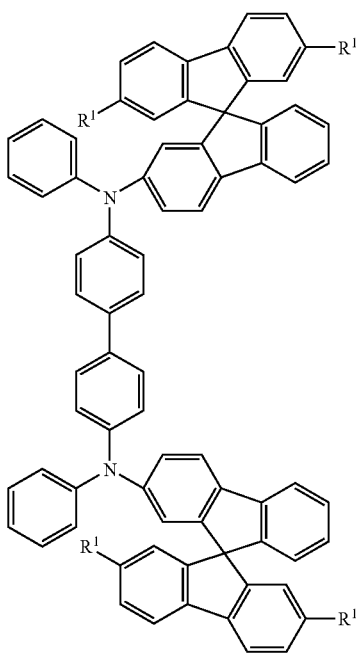

(1)

wherein R¹ is hydrogen or an alkyl group having carbon atoms 1-4.

8. A light emitting device comprising a light emitting element,
wherein the light emitting element comprises a layer including a benzidine derivative represented by a general formula (2) between a pair of electrodes (2)

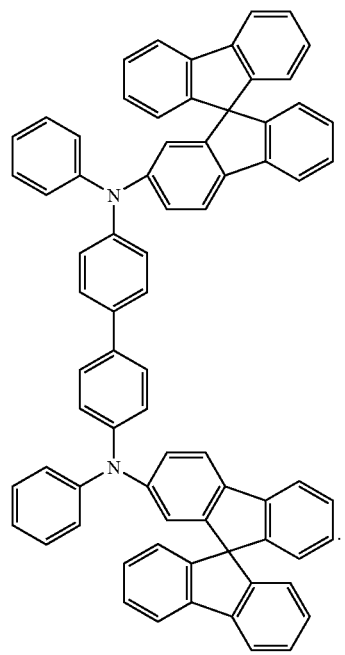

9. A light emitting device comprising a light emitting element,
wherein the light emitting element comprises a layer including a benzidine derivative between a pair of electrodes,
wherein the benzidine derivative is obtained by a coupling reaction of N,N'-diphenylbenzidine with 2-bromo-spiro-9,9'-bifluorene, and wherein the benzidine derivative has a melting point of from 323 to 324° C.

10. The light emitting device according to any one of claims 7 to 9, wherein the layer is provided as a hole transporting layer.

11. An electric appliance having a light emitting device comprising a light emitting element in a display portion,
wherein the light emitting element comprising a layer including a benzidine derivative represented by a general formula (1) between a pair of electrodes (1)

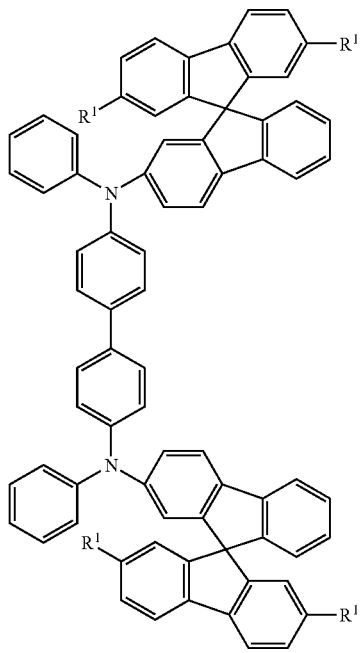

wherein R¹ is hydrogen or an alkyl group having carbon atoms 1-4.

12. An electric appliance having a light emitting device comprising a light emitting element in a display portion,
wherein the light emitting element comprising a layer including a benzidine derivative represented by a general formula (2) between a pair of electrodes (2)

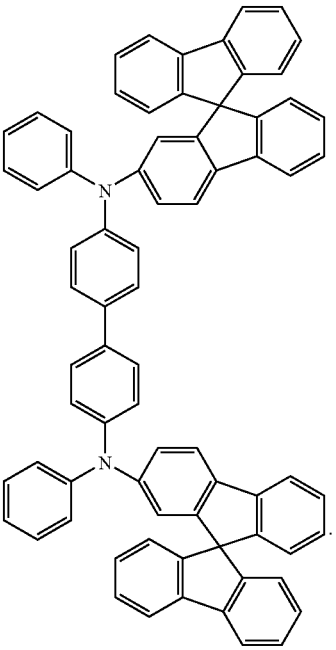

13. An electric appliance having a light emitting device comprising a light emitting element in a display portion,
   wherein the light emitting element comprising a layer including a benzidine derivative between a pair of electrodes,
   wherein the benzidine derivative is obtained by a coupling reaction of N,N'-diphenylbenzidine with 2-bromo-spiro-9,9'-bifluorene, and
   wherein the benzidine derivative has a melting point of from 323 to 324° C.

14. The electric appliance according to any one of claims 11 to 13 wherein the layer is provided as a hole transporting layer.

* * * * *